(12) United States Patent
Moore et al.

(10) Patent No.: US 11,141,317 B2
(45) Date of Patent: Oct. 12, 2021

(54) WOUND THERAPY SYSTEM WITH WOUND VOLUME ESTIMATION

(71) Applicant: KCI LICENSING, INC., San Antonio, TX (US)

(72) Inventors: Brett L. Moore, San Antonio, TX (US); Shannon C. Ingram, Bulverde, TX (US); Justin R. Rice, San Antonio, TX (US)

(73) Assignee: KCI LICENSING, INC., San Antonio, TX (US)

(*) Notice: Subject to any disclaimer, the term of this patent is extended or adjusted under 35 U.S.C. 154(b) by 276 days.

(21) Appl. No.: 16/363,763

(22) Filed: Mar. 25, 2019

(65) Prior Publication Data
US 2019/0298579 A1 Oct. 3, 2019

Related U.S. Application Data

(60) Provisional application No. 62/650,132, filed on Mar. 29, 2018, provisional application No. 62/799,241, filed on Jan. 31, 2019.

(51) Int. Cl.
*A61M 1/00* (2006.01)
*A61F 13/02* (2006.01)
(Continued)

(52) U.S. Cl.
CPC ........ *A61F 13/0216* (2013.01); *A61B 5/1073* (2013.01); *A61B 5/1076* (2013.01);
(Continued)

(58) Field of Classification Search
CPC ........ A61F 13/0216; A61F 2013/00174; A61F 2013/8494; A61M 1/009; A61M 1/0092;
(Continued)

(56) References Cited

U.S. PATENT DOCUMENTS 1,355,846 A   10/1920  Rannells
2,547,758 A    4/1951  Keeling
(Continued)

FOREIGN PATENT DOCUMENTS

AU   550575 B2   3/1986
AU   745271 B2   3/2002
(Continued)

OTHER PUBLICATIONS

International Search Report and Written Opinion in International Application No. PCT/US2019/023904, dated Sep. 9, 2019. (20 pages).

(Continued)

*Primary Examiner* — Nicholas J Weiss
*Assistant Examiner* — Gregory J Feulner
(74) *Attorney, Agent, or Firm* — Foley & Lardner LLP

(57) ABSTRACT

A wound therapy system includes a negative pressure circuit configured to apply negative pressure to a wound, a pump fluidly coupled to the negative pressure circuit and operable to control the negative pressure within the negative pressure circuit, a pressure sensor configured to measure the negative pressure within the negative pressure circuit or at the wound and a controller communicably coupled to the pump and the pressure sensor. The controller is configured to execute a pressure testing procedure including applying a pressure stimulus to the negative pressure circuit, observe a dynamic pressure response of the negative pressure circuit to the pressure stimulus using pressure measurements recorded by the pressure sensor, and estimate a wound volume of the wound based on the dynamic pressure response.

36 Claims, 12 Drawing Sheets

(51) Int. Cl.
  *A61B 5/00* (2006.01)
  *A61M 3/02* (2006.01)
  *A61B 5/107* (2006.01)
  *A61F 13/40* (2006.01)
  *A61F 13/00* (2006.01)
  *A61F 13/84* (2006.01)

(52) U.S. Cl.
  CPC ........... *A61B 5/445* (2013.01); *A61M 1/0023* (2013.01); *A61M 1/0058* (2013.01); *A61M 1/73* (2021.05); *A61M 1/85* (2021.05); *A61M 1/90* (2021.05); *A61M 1/962* (2021.05); *A61M 1/964* (2021.05); *A61M 3/022* (2014.02); *A61M 3/0258* (2013.01); *A61F 2013/00174* (2013.01); *A61F 2013/8494* (2013.01); *A61M 1/742* (2021.05); *A61M 35/006* (2013.01); *A61M 2205/15* (2013.01); *A61M 2205/3331* (2013.01); *A61M 2205/3334* (2013.01); *A61M 2205/3337* (2013.01); *A61M 2205/3344* (2013.01); *A61M 2205/3379* (2013.01); *A61M 2205/702* (2013.01)

(58) Field of Classification Search
  CPC .............. A61M 1/0023; A61M 35/006; A61M 2205/3337; A61M 2205/3344; A61M 2205/52; A61M 1/0084; A61M 1/0058; A61M 2205/3334; A61M 1/0033; A61M 3/0258; A61M 3/022; A61M 1/0025; A61B 5/445; A61B 5/1073
  See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 8,814,841 B2 | 8/2014 | Hartwell | |
| 9,192,332 B2 | 11/2015 | Hartwell | |
| 9,987,402 B2 | 6/2018 | Hartwell | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2015/0032031 A1 | 1/2015 | Hartwell | |
| 2016/0287763 A1* | 10/2016 | Simmons | A61M 1/73 |
| 2016/0325028 A1* | 11/2016 | Locke | A61M 1/90 |
| 2016/0354535 A1* | 12/2016 | Blott | A61N 5/025 |
| 2016/0361475 A1* | 12/2016 | Heaton | A61M 1/90 |
| 2017/0296715 A1* | 10/2017 | Weston | A61M 1/0031 |
| 2018/0042521 A1* | 2/2018 | Ryu | A61B 5/1073 |
| 2018/0050137 A1* | 2/2018 | Ryu | A61M 27/00 |
| 2018/0369456 A1 | 12/2018 | Hartwell | |
| 2020/0376175 A1* | 12/2020 | Hartwell | A61M 1/73 |

(56) References Cited

U.S. PATENT DOCUMENTS

FOREIGN PATENT DOCUMENTS

| AU | 755496 B2 | 12/2002 |
|---|---|---|
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 3 269 404 A1 | 1/2018 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO 2009/071924 A1 | 6/2009 |

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospherlc Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds In Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its

(56) References Cited

OTHER PUBLICATIONS

Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

WOUND THERAPY SYSTEM WITH WOUND VOLUME ESTIMATION

CROSS-REFERENCE TO RELATED APPLICATIONS

This application claims the benefit of priority to U.S. Provisional Application No. 62/650,132, filed on Mar. 29, 2018, and U.S. Provisional Application No. 62/799,241, filed on Jan. 31, 2019, the complete disclosures of which are each incorporated herein by reference in their entireties.

BACKGROUND

The present disclosure relates generally to a wound therapy system, and more particularly to a wound therapy system configured to estimate the volume of a wound.

Negative pressure wound therapy (NPWT) is a type of wound therapy that involves applying a negative pressure to a wound site to promote wound healing. Some wound treatment systems apply negative pressure to a wound using a pneumatic pump to generate the negative pressure and flow required. Recent advancements in wound healing with NPWT involve applying topical fluids to wounds to work in combination with NPWT. However, it can be difficult to determine the appropriate volume of instillation fluid to deliver to the wound. Additionally, it can be difficult to accurately monitor and track healing progression over time.

SUMMARY

One implementation of the present disclosure is a wound therapy system including a negative pressure circuit configured to apply negative pressure to a wound, a pump fluidly coupled to the negative pressure circuit and operable to control the negative pressure within the negative pressure circuit, a pressure sensor configured to measure the negative pressure within the negative pressure circuit or at the wound and a controller communicably coupled to the pump and the pressure sensor. The controller is configured to execute a pressure testing procedure including applying a pressure stimulus to the negative pressure circuit, observe a dynamic pressure response of the negative pressure circuit to the pressure stimulus using pressure measurements recorded by the pressure sensor, and estimate a wound volume of the wound based on the dynamic pressure response.

In some embodiments, the negative pressure circuit includes a wound dressing sealable to skin surrounding the wound. In some embodiments, the negative pressure circuit includes at least one of an instillation fluid canister containing instillation fluid for delivery to the wound or a removed fluid canister containing fluid removed from the wound. In some embodiments, the negative pressure circuit includes tubing fluidly connecting the pump with the wound.

In some embodiments, the negative pressure circuit includes a wound dressing sealable to skin surrounding the wound, at least one of an instillation fluid canister containing instillation fluid for delivery to the wound or a removed fluid canister containing fluid removed from the wound, and tubing fluidly connecting the instillation fluid canister or the removed fluid canister with the wound dressing.

In some embodiments, the controller is configured to operate the pump to establish the negative pressure within the negative pressure circuit. In some embodiments, the testing procedure includes operating the pump to establish the negative pressure within the negative pressure circuit and applying the pressure stimulus after the negative pressure has been established within the negative pressure circuit.

In some embodiments, the system includes a valve coupled to the negative pressure circuit and operable to controllably vent the negative pressure circuit. In some embodiments, applying the pressure stimulus includes opening the valve to allow airflow into the negative pressure circuit for a predetermined amount of time and closing the valve after the predetermined amount of time has elapsed. In some embodiments, applying the pressure stimulus further includes waiting for another predetermined amount of time after closing the valve and repeating the opening, closing, and waiting steps until the negative pressure reaches a threshold pressure value. In some embodiments, applying the pressure stimulus further includes operating the pump while the valve is closed to mitigate air leakage into the negative pressure circuit.

In some embodiments, the dynamic pressure response of the negative pressure circuit is characterized by a depth of purge parameter defined as a difference between a measured value of the negative pressure before the valve is opened and a measured value of the negative pressure while the valve is open.

In some embodiments, the dynamic pressure response of the negative pressure circuit is characterized by a rebound parameter defined as a difference between a measured value of the negative pressure after the valve is closed and a measured value of the negative pressure while the valve is open.

In some embodiments, the dynamic pressure response of the negative pressure circuit is characterized by a delta parameter defined as a difference between a measured value of the negative pressure before the valve is opened and a measured value of the negative pressure after the valve is closed.

In some embodiments, the dynamic pressure response of the negative pressure circuit is characterized by a leak rate parameter defined as a rate at which the negative pressure changes while the valve is closed.

In some embodiments, the wound therapy system includes an orifice located along the negative pressure circuit and configured to allow air to leak into the negative pressure circuit at a known rate.

In some embodiments, applying the pressure stimulus includes operating the pump to achieve a predetermined negative pressure within the negative pressure circuit and deactivating the pump upon reaching the predetermined negative pressure within the negative pressure circuit.

In some embodiments, estimating the wound volume based on the dynamic pressure response includes determining values for one or more parameters that characterize the dynamic pressure response and applying the values of the one or more parameters as inputs to a model that defines a relationship between the one or more parameters and the wound volume.

In some embodiments, the model that defines the relationship between the one or more parameters and the wound volume is a polynomial approximation model. In some embodiments, the model that defines the relationship between the one or more parameters and the wound volume is a neural network.

In some embodiments, the controller is configured to generate the model that defines the relationship between the one or more parameters and the wound volume by executing a training procedure comprising applying the pressure stimulus to training circuit having a known volume, observing a dynamic pressure response of the training circuit to the pressure stimulus using pressure measurements recorded by the pressure sensor and associating the known volume with the dynamic pressure response of the training circuit.

In some embodiments, generating the model further includes repeating the training procedure for a plurality of known volumes, observing the dynamic pressure response of the training circuit for each of the plurality of known volumes, and generating a correlation between the plurality of known volumes and the dynamic pressure response of the training circuit.

In some embodiments, the controller is configured to execute the pressure testing procedure, observe the dynamic pressure response, and estimate the wound volume at a plurality of times during wound treatment. The controller can be configured to determine healing progression based on changes in the wound volume during wound treatment.

In some embodiments, the controller is configured to determine a volume of instillation fluid to deliver to the wound based on the estimated wound volume. The controller can be configured to operate the pump to deliver the volume of instillation fluid to the wound.

In some embodiments, the controller is configured to determine the volume of instillation fluid to deliver to the wound by multiplying the estimated wound volume by a fluid instillation factor. In some embodiments, the fluid instillation factor is less than one such that less than the total wound volume is filled with the instillation fluid. In some embodiments, the fluid instillation factor is between approximately 0.2 and approximately 0.8.

Another implementation of the present disclosure is a method for estimating a wound volume of a wound. The method includes applying negative pressure to a wound using a negative pressure circuit, operating a pump fluidly coupled to the negative pressure circuit to control the negative pressure within the negative pressure circuit, measuring the negative pressure within the negative pressure circuit or at the wound, executing a pressure testing procedure including applying a pressure stimulus to the negative pressure circuit, observing a dynamic pressure response of the negative pressure circuit to the pressure stimulus using measurements of the negative pressure, and estimating the wound volume based on the dynamic pressure response.

In some embodiments, the negative pressure circuit includes a wound dressing sealable to skin surrounding the wound. In some embodiments, the negative pressure circuit includes at least one of an instillation fluid canister containing instillation fluid for delivery to the wound or a removed fluid canister containing fluid removed from the wound. In some embodiments, the negative pressure circuit includes tubing fluidly connecting the pump with the wound.

In some embodiments, the negative pressure circuit includes a wound dressing sealable to skin surrounding the wound, at least one of an instillation fluid canister containing instillation fluid for delivery to the wound or a removed fluid canister containing fluid removed from the wound, and tubing fluidly connecting the instillation fluid canister or the removed fluid canister with the wound dressing.

In some embodiments, the method includes operating the pump to establish the negative pressure within the negative pressure circuit. In some embodiments, the testing procedure includes operating the pump to establish the negative pressure within the negative pressure circuit and applying the pressure stimulus after the negative pressure has been established within the negative pressure circuit.

In some embodiments, the method includes operating a valve coupled to the negative pressure circuit to controllably vent the negative pressure circuit. In some embodiments, applying the pressure stimulus includes opening the valve to allow airflow into the negative pressure circuit for a predetermined amount of time and closing the valve after the predetermined amount of time has elapsed.

In some embodiments, applying the pressure stimulus further includes waiting for another predetermined amount of time after closing the valve and repeating the opening, closing, and waiting steps until the negative pressure reaches a threshold pressure value. In some embodiments, applying the pressure stimulus further includes operating the pump while the valve is closed to mitigate air leakage into the negative pressure circuit.

In some embodiments, the dynamic pressure response of the negative pressure circuit is characterized by a depth of purge parameter defined as a difference between a measured value of the negative pressure before the valve is opened and a measured value of the negative pressure while the valve is open.

In some embodiments, the dynamic pressure response of the negative pressure circuit is characterized by a rebound parameter defined as a difference between a measured value of the negative pressure after the valve is closed and a measured value of the negative pressure while the valve is open.

In some embodiments, the dynamic pressure response of the negative pressure circuit is characterized by a delta parameter defined as a difference between a measured value of the negative pressure before the valve is opened and a measured value of the negative pressure after the valve is closed.

In some embodiments, the dynamic pressure response of the negative pressure circuit is characterized by a leak rate parameter defined as a rate at which the negative pressure changes while the valve is closed.

In some embodiments, the method includes allowing air to leak into the negative pressure circuit at a known rate via an orifice located along the negative pressure circuit.

In some embodiments, applying the pressure stimulus includes operating the pump to achieve a predetermined negative pressure within the negative pressure circuit and deactivating the pump upon reaching the predetermined negative pressure within the negative pressure circuit.

In some embodiments, estimating the wound volume based on the dynamic pressure response includes determining values for one or more parameters that characterize the dynamic pressure response and applying the values of the one or more parameters as inputs to a model that defines a relationship between the one or more parameters and the wound volume.

In some embodiments, the model that defines the relationship between the one or more parameters and the wound volume is a polynomial approximation model. In some embodiments, the model that defines the relationship between the one or more parameters and the wound volume is a neural network.

In some embodiments, the method includes generating the model that defines the relationship between the one or more parameters and the wound volume by executing a training procedure comprising applying the pressure stimulus to training circuit having a known volume, observing a dynamic pressure response of the training circuit to the pressure stimulus using pressure measurements recorded by the pressure sensor, and associating the known volume with the dynamic pressure response of the training circuit.

In some embodiments, generating the model further includes repeating the training procedure for a plurality of known volumes, observing the dynamic pressure response of the training circuit for each of the plurality of known volumes, and generating a correlation between the plurality of known volumes and the dynamic pressure response of the training circuit.

In some embodiments, the method includes executing the pressure testing procedure, observing the dynamic pressure response, and estimating the wound volume at a plurality of times during wound treatment. The method may include determining healing progression based on changes in the wound volume during wound treatment.

In some embodiments, the method includes determining a volume of instillation fluid to deliver to the wound based on the estimated wound volume and operating the pump to deliver the volume of instillation fluid to the wound.

In some embodiments, determining the volume of instillation fluid to deliver to the wound includes multiplying the estimated wound volume by a fluid instillation factor. In some embodiments, the fluid instillation factor is less than one such that less than the total wound volume is filled with the instillation fluid. In some embodiments, the fluid instillation factor is between approximately 0.2 and approximately 0.8.

Another implementation of the present disclosure is wound therapy system. The wound therapy system includes a negative pressure circuit configured to apply negative pressure to a wound, a canister containing instillation fluid for delivery to the wound, a pump operable to deliver the instillation fluid to the wound, a pressure sensor configured to measure the negative pressure within the negative pressure circuit or at the wound, and a controller communicably coupled to the pump and the pressure sensor. The controller is configured to execute a pressure testing procedure to estimate a wound volume of the wound, determine a volume of instillation fluid to deliver to the wound based on the estimated wound volume, and operate the pump to deliver the volume of instillation fluid to the wound.

In some embodiments, the controller is configured to determine the volume of instillation fluid to deliver to the wound by multiplying the estimated wound volume by a fluid instillation factor. In some embodiments, the fluid instillation factor is less than one such that less than the total wound volume is filled with the instillation fluid. In some embodiments, the fluid instillation factor is between approximately 0.2 and approximately 0.8.

In some embodiments, the negative pressure circuit includes a wound dressing sealable to skin surrounding the wound. In some embodiments, the negative pressure circuit includes tubing fluidly connecting the canister with the wound dressing.

In some embodiments, the controller is configured to operate the pump to establish the negative pressure within the negative pressure circuit. In some embodiments, the pressure testing procedure includes operating the pump to establish the negative pressure within the negative pressure circuit and applying a pressure stimulus to the negative pressure circuit after the negative pressure has been established within the negative pressure circuit.

In some embodiments, the wound therapy system includes an orifice located along the negative pressure circuit and configured to allow air to leak into the negative pressure circuit at a known rate.

In some embodiments, the pressure testing procedure includes operating the pump to achieve a predetermined negative pressure within the negative pressure circuit and, upon reaching the predetermined negative pressure within the negative pressure circuit, deactivating the pump and observing a dynamic pressure response of the negative pressure circuit.

In some embodiments, the system includes a valve coupled to the negative pressure circuit and operable to controllably vent the negative pressure circuit. In some embodiments, the pressure testing procedure includes opening the valve to allow airflow into the negative pressure circuit for a predetermined amount of time and closing the valve after the predetermined amount of time has elapsed.

In some embodiments, the pressure testing procedure includes waiting for another predetermined amount of time after closing the valve and repeating the opening, closing, and waiting steps until the negative pressure reaches a threshold pressure value.

In some embodiments, the pressure testing procedure includes applying a pressure stimulus to the negative pressure circuit, observing a dynamic pressure response of the negative pressure circuit to the pressure stimulus using pressure measurements recorded by the pressure sensor, and estimating the wound volume of the wound based on the dynamic pressure response. In some embodiments, the pressure testing procedure includes operating the pump while the valve is closed to mitigate air leakage into the negative pressure circuit.

In some embodiments, the dynamic pressure response of the negative pressure circuit is characterized by a depth of purge parameter defined as a difference between a measured value of the negative pressure before the valve is opened and a measured value of the negative pressure while the valve is open.

In some embodiments, the dynamic pressure response of the negative pressure circuit is characterized by a rebound parameter defined as a difference between a measured value of the negative pressure after the valve is closed and a measured value of the negative pressure while the valve is open.

In some embodiments, the dynamic pressure response of the negative pressure circuit is characterized by a delta parameter defined as a difference between a measured value of the negative pressure before the valve is opened and a measured value of the negative pressure after the valve is closed.

In some embodiments, the dynamic pressure response of the negative pressure circuit is characterized by a leak rate parameter defined as a rate at which the negative pressure changes while the valve is closed.

In some embodiments, estimating the wound volume based on the dynamic pressure response includes determining values for one or more parameters that characterize the dynamic pressure response and applying the values of the one or more parameters as inputs to a model that defines a relationship between the one or more parameters and the wound volume.

In some embodiments, the model that defines the relationship between the one or more parameters and the wound volume is a polynomial approximation model. In some embodiments, the model that defines the relationship between the one or more parameters and the wound volume is a neural network.

In some embodiments, the controller is configured to generate the model that defines the relationship between the one or more parameters and the wound volume by executing a training procedure comprising applying the pressure stimulus to training circuit having a known volume, observing a dynamic pressure response of the training circuit to the pressure stimulus using pressure measurements recorded by the pressure sensor, and associating the known volume with the dynamic pressure response of the training circuit.

In some embodiments, generating the model further includes repeating the training procedure for a plurality of known volumes, observing the dynamic pressure response of the training circuit for each of the plurality of known volumes, and generating a correlation between the plurality of known volumes and the dynamic pressure response of the training circuit.

In some embodiments, the controller is configured to execute the pressure testing procedure to estimate the wound volume at a plurality of times during wound treatment and determine healing progression based on changes in the wound volume during wound treatment.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

DETAILED DESCRIPTION

Overview

Figure 1:
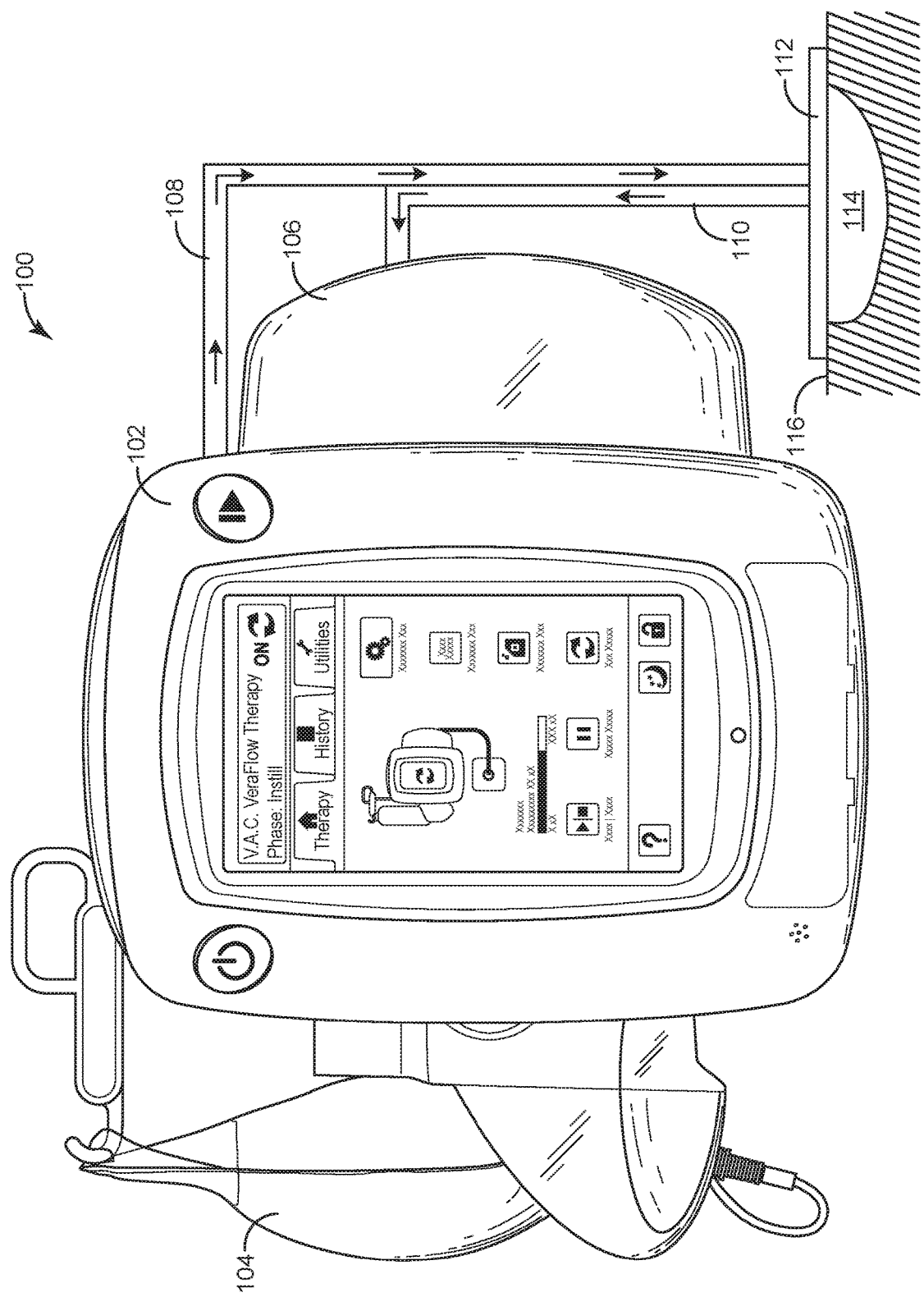
FIG. 1 is a block diagram of a wound therapy system including a therapy device coupled to a wound dressing via tubing, according to an exemplary embodiment.

Referring generally to the FIGURES, a wound therapy system with fluid instillation and removal and components thereof are shown, according to various exemplary embodiments. The wound therapy system may include a therapy device and a wound dressing. The therapy device may include an instillation fluid canister, a removed fluid canister, a valve, a pneumatic pump, an installation pump, and a controller. The wound dressing can be applied to a patient's skin surrounding a wound. The therapy device can be configured to deliver instillation fluid to the wound and provide negative pressure wound therapy (NPWT) by maintaining the wound at negative pressure. Components of the wound therapy device, the wound dressing, and/or the wound form a negative pressure circuit.

The controller can be configured to operate the pneumatic pump, the instillation pump, the valve, and/or other controllable components of the therapy device. In some embodiments, the controller performs a pressure testing procedure by applying a pressure stimulus to the negative pressure circuit. For example, the controller may instruct the valve to close and operate the pneumatic pump to establish negative pressure within the negative pressure circuit. Once the negative pressure has been established, the controller may deactivate the pneumatic pump. The controller may cause the valve to open for a predetermined amount of time and then close after the predetermined amount of time has elapsed. In some embodiments, the controller operates the pneumatic pump while the valve is closed to mitigate air leakage into the negative pressure circuit. The controller may observe a dynamic pressure response of the negative pressure circuit to the pressure stimulus using pressure measurements recorded by a pressure sensor. The dynamic pressure response may be characterized by a variety of parameters including, for example, a depth of purge parameter, a rebound parameter, a delta parameter, and a leak rate parameter (described in greater detail below).

The controller can estimate the volume of the wound based on the observed dynamic pressure response. For example, the controller can apply the observed parameters as inputs to a pressure model that defines a relationship between the observed parameters and the volume of the negative pressure circuit and/or the volume of the wound. The model may include a polynomial approximation model, a neural network model, or any other model that relates the observed parameters to the volume of the negative pressure circuit and/or the volume of the wound. In some embodiments, the pressure model is a pre-existing model stored in the controller by the manufacturer of the therapy device. In other embodiments, the controller can generate the pressure model on-site by performing a training procedure.

The training procedure may be the same as the pressure testing procedure with the exception that the therapy device is connected to a training circuit having a known volume. For example, the wound dressing can be applied to a test device having a known volume rather than to a patient's skin surrounding a wound. The controller can apply the pressure stimulus to various training circuits having various known volumes and may observe the dynamic pressure response of each training circuit. Each of the known volumes may result in a different dynamic pressure response to the pressure stimulus. The controller can then associate the known volume of each training circuit with the corresponding dynamic pressure response. In some embodiments, the controller uses the dynamic pressure responses of the training circuits to generate the pressure model that defines a relationship between the observed parameters of the dynamic pressure response (e.g., depth of purge, rebound, delta, leak rate, etc.) and the volume of the training circuit. The pressure model can then be stored in the therapy device and used to estimate the volume of a wound, as previously described.

In some embodiments, the controller is configured to execute the pressure testing procedure, observe the dynamic pressure response, and estimate the wound volume at a plurality of times during wound treatment. The controller can then determine healing progression based on changes in the wound volume during wound treatment. In some embodiments, the controller is configured to determine a volume of instillation fluid to deliver to the wound based on the estimated wound volume. The volume of instillation fluid to deliver may be a predetermined percentage of the volume of the wound (e.g., 20%, 50%, 80%, etc.). The controller can then operate the instillation pump to deliver the determined volume of instillation fluid to the wound. These and other features of the wound therapy system are described in detail below.

Wound Therapy System

Referring now to FIGS. 1-4, a negative pressure wound therapy (NPWT) system 100 is shown, according to an exemplary embodiment. NPWT system 100 is shown to include a therapy device 102 fluidly connected to a wound dressing 112 via tubing 108 and 110. Wound dressing 112 may be adhered or sealed to a patient's skin 116 surrounding a wound 114. Several examples of wound dressings 112 which can be used in combination with NPWT system 100 are described in detail in U.S. Pat. No. 7,651,484 granted Jan. 26, 2010, U.S. Pat. No. 8,394,081 granted Mar. 12, 2013, and U.S. patent application Ser. No. 14/087,418 filed Nov. 22, 2013. The entire disclosure of each of these patents and patent applications is incorporated by reference herein.

Therapy device 102 can be configured to provide negative pressure wound therapy by reducing the pressure at wound 114. Therapy device 102 can draw a vacuum at wound 114 (relative to atmospheric pressure) by removing wound exudate, air, and other fluids from wound 114. Wound exudate may include fluid that filters from a patient's circulatory system into lesions or areas of inflammation. For example, wound exudate may include water and dissolved solutes such as blood, plasma proteins, white blood cells, platelets, and red blood cells. Other fluids removed from wound 114 may include instillation fluid 105 previously delivered to wound 114. Instillation fluid 105 can include, for example, a cleansing fluid, a prescribed fluid, a medicated fluid, an antibiotic fluid, or any other type of fluid which can be delivered to wound 114 during wound treatment. Instillation fluid 105 may be held in an instillation fluid canister 104 and controllably dispensed to wound 114 via instillation fluid tubing 108. In some embodiments, instillation fluid canister 104 is detachable from therapy device 102 to allow canister 106 to be refilled and replaced as needed.

The fluids 107 removed from wound 114 pass through removed fluid tubing 110 and are collected in removed fluid canister 106. Removed fluid canister 106 may be a component of therapy device 102 configured to collect wound exudate and other fluids 107 removed from wound 114. In some embodiments, removed fluid canister 106 is detachable from therapy device 102 to allow canister 106 to be emptied and replaced as needed. A lower portion of canister 106 may be filled with wound exudate and other fluids 107 removed from wound 114, whereas an upper portion of canister 106 may be filled with air. Therapy device 102 can be configured to draw a vacuum within canister 106 by pumping air out of canister 106. The reduced pressure within canister 106 can be translated to wound dressing 112 and wound 114 via tubing 110 such that wound dressing 112 and wound 114 are maintained at the same pressure as canister 106.

Figure 2:
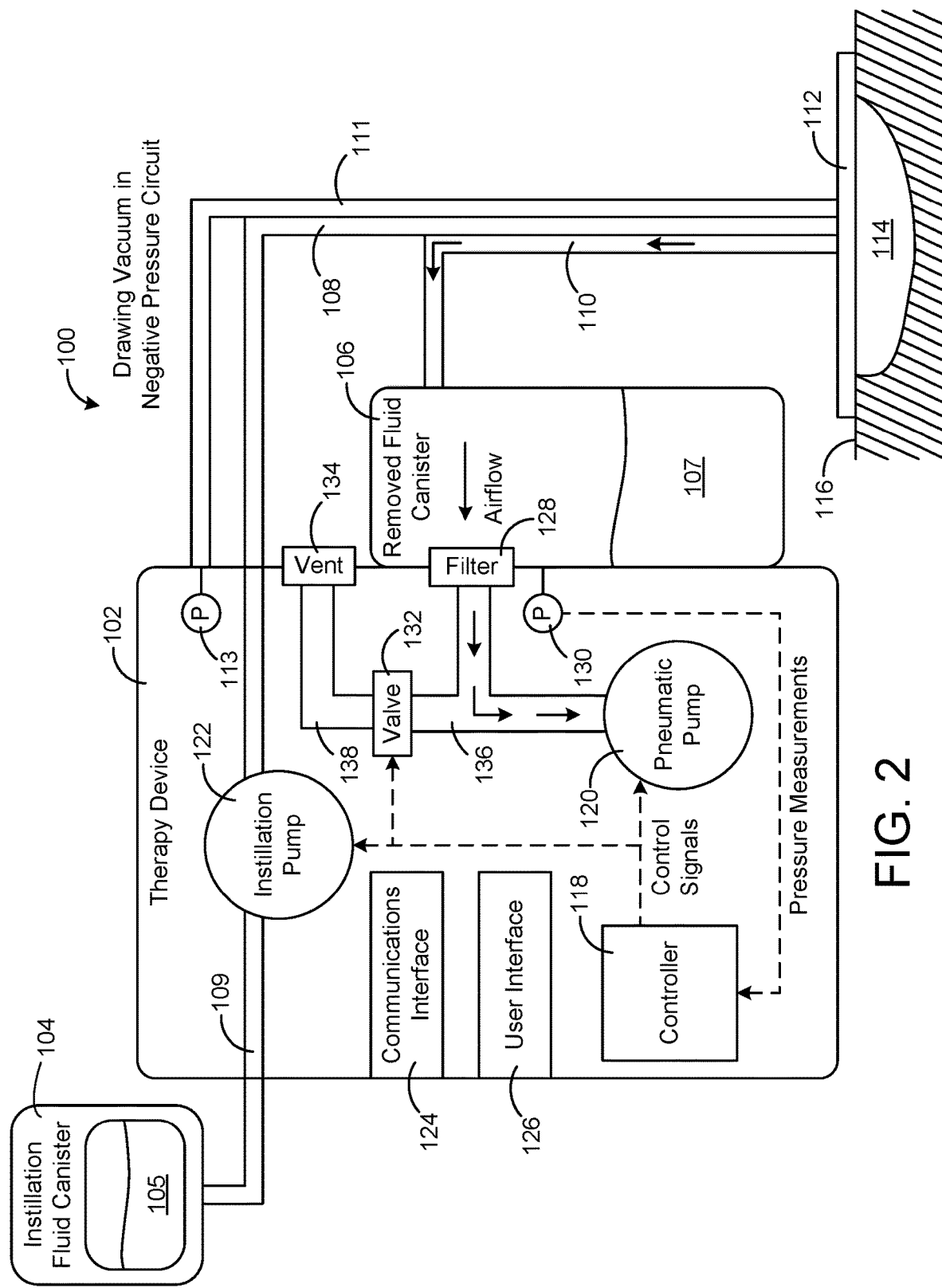
FIG. 2 is a block diagram illustrating the therapy device of FIG. 1 in greater detail when the therapy device operates to draw a vacuum within a negative pressure circuit, according to an exemplary embodiment.
Figure 3A:
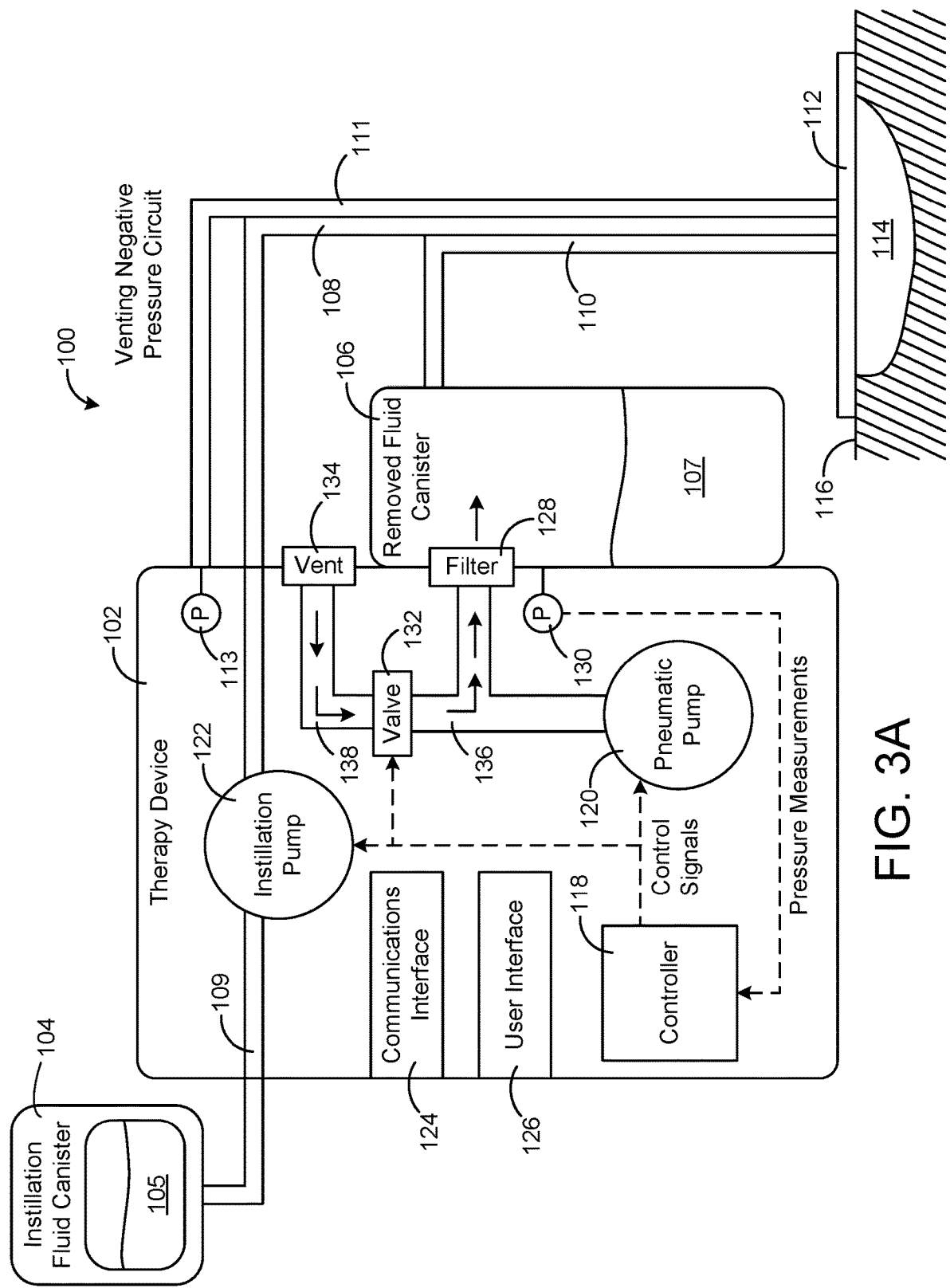
FIG. 3A is a block diagram illustrating the therapy device of FIG. 1 in greater detail when the therapy device operates to vent the negative pressure circuit, according to an exemplary embodiment.
Figure 3B:
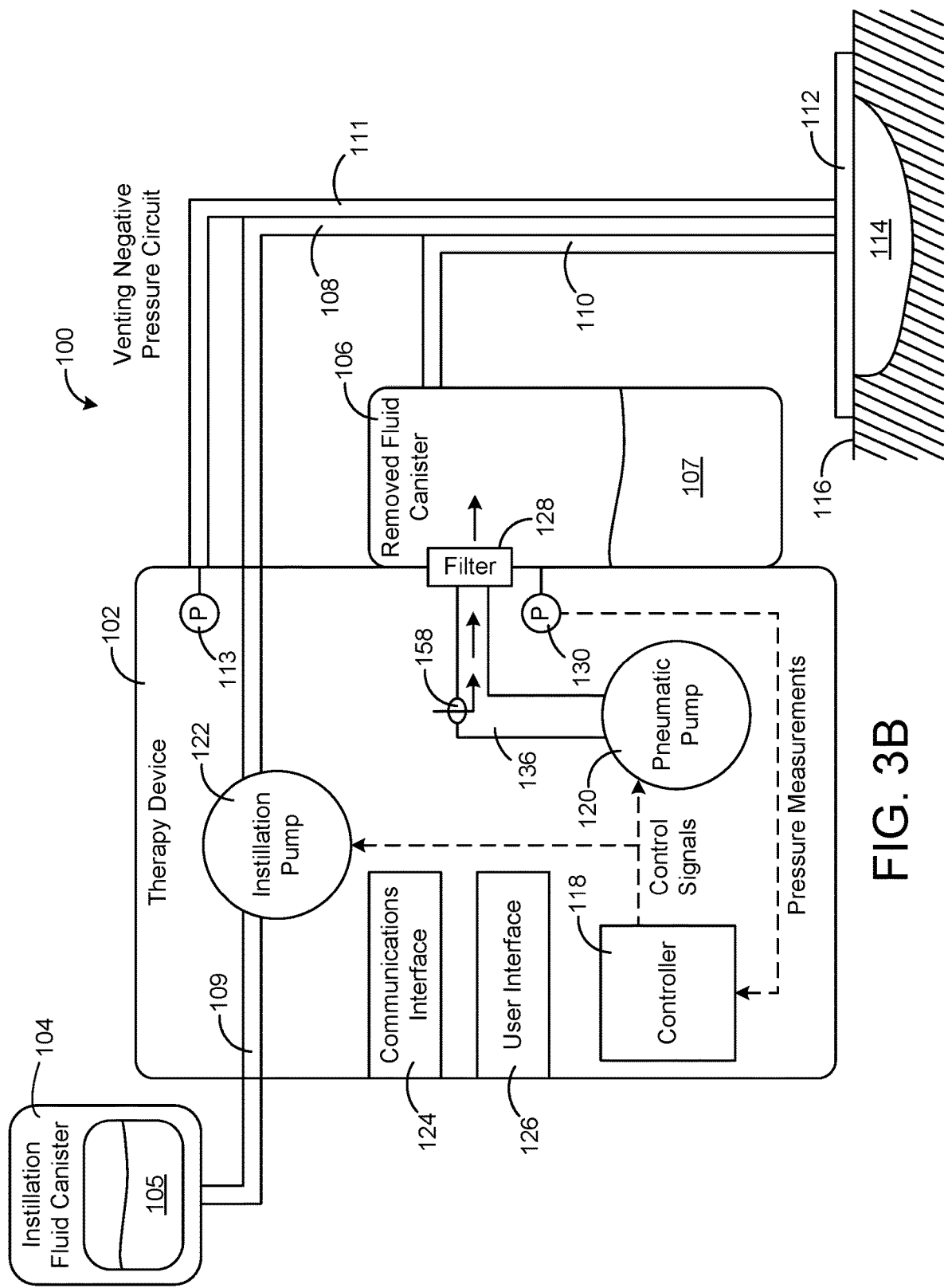
FIG. 3B is a block diagram illustrating the therapy device of FIG. 1 in greater detail when the therapy device uses an orifice to vent the negative pressure circuit, according to an exemplary embodiment.
Figure 4:
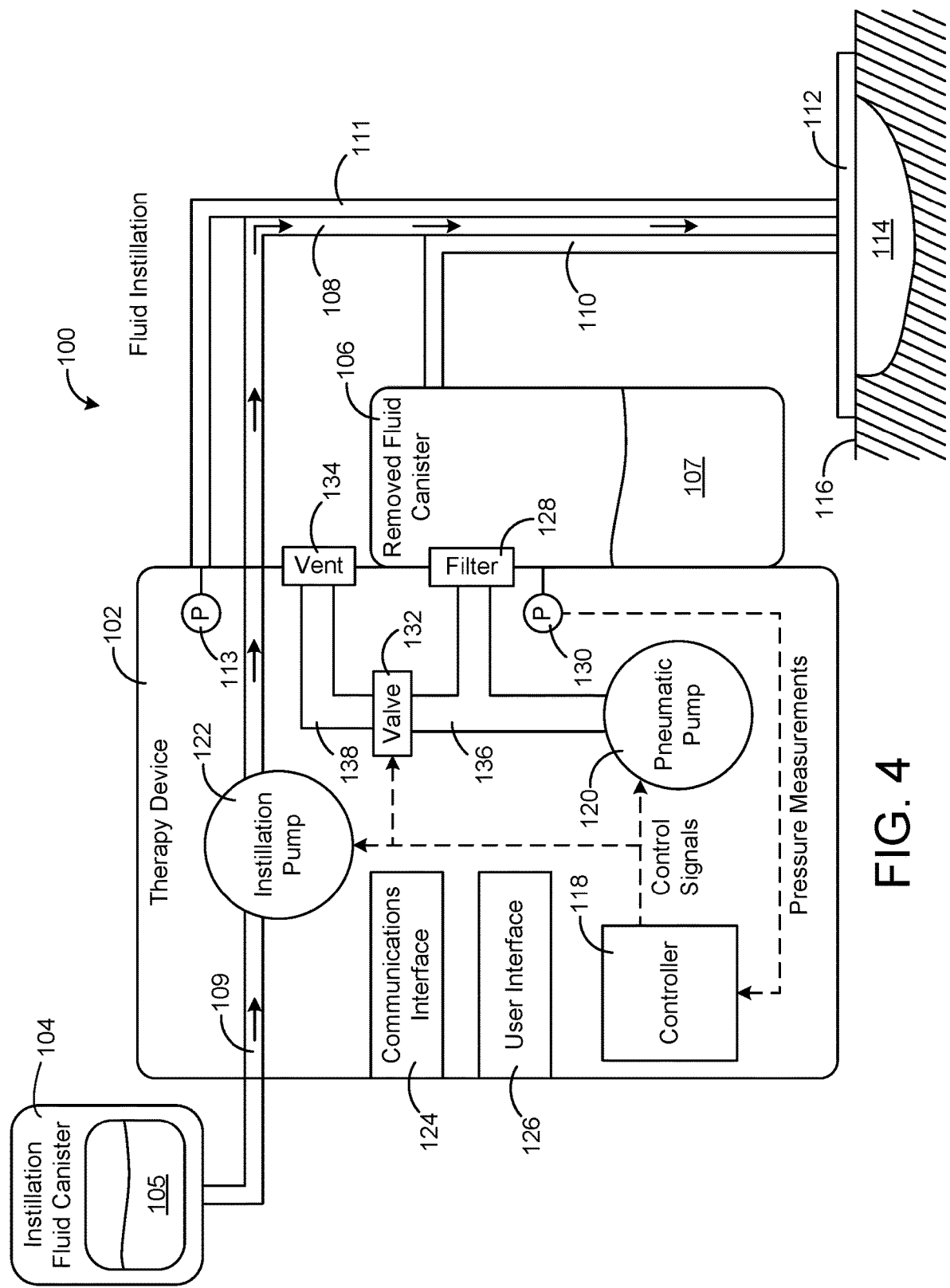
FIG. 4 is a block diagram illustrating the therapy device of FIG. 1 in greater detail when the therapy device operates to deliver instillation fluid to the wound dressing and/or a wound, according to an exemplary embodiment.
Figure 5:
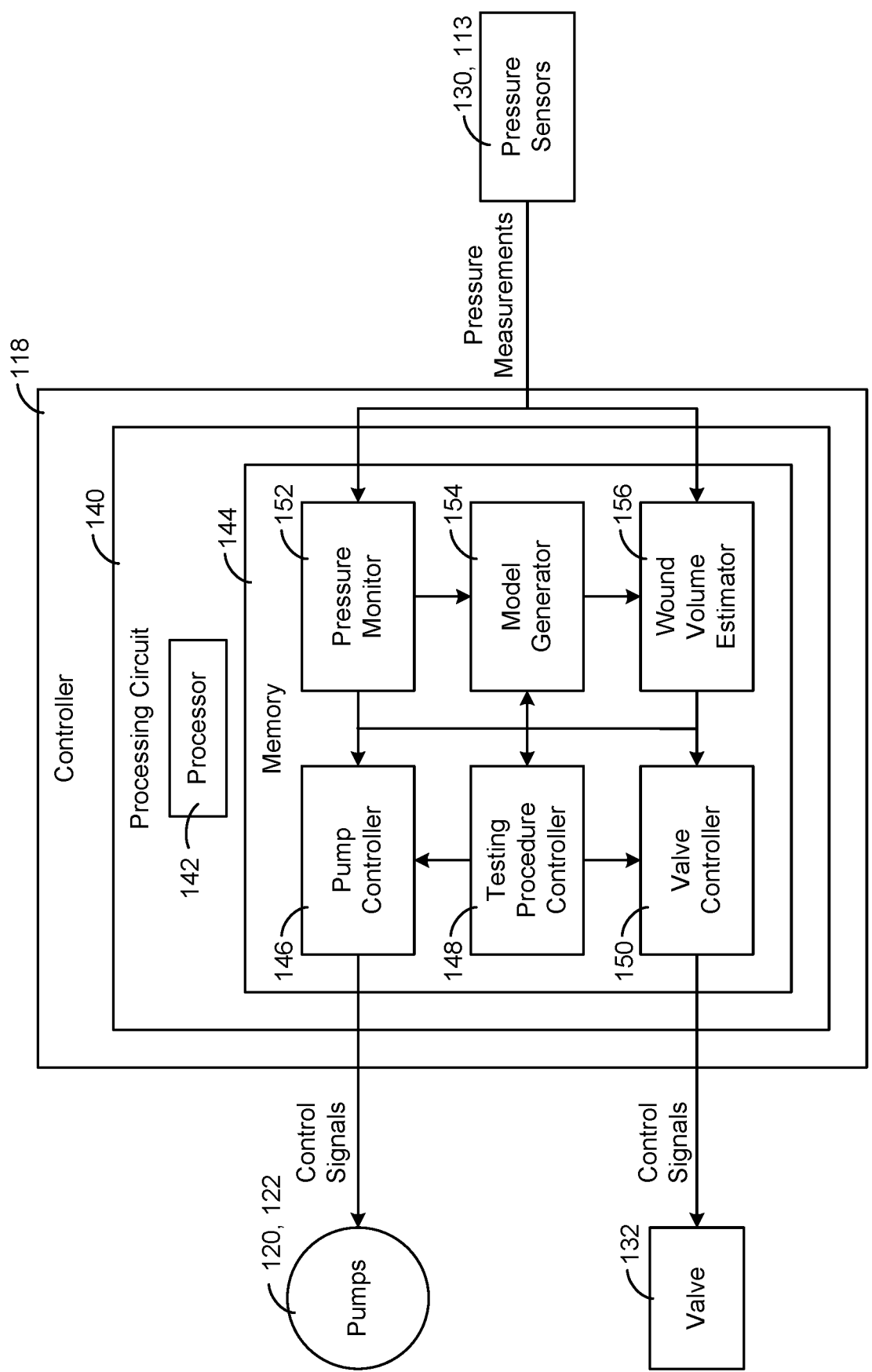
FIG. 5 is a block diagram illustrating a controller of the therapy device of FIG. 1 in greater detail, according to an exemplary embodiment.

Referring particularly to FIGS. 2-4, block diagrams illustrating therapy device 102 in greater detail are shown, according to an exemplary embodiment. Therapy device 102 is shown to include a pneumatic pump 120, an instillation pump 122, a valve 132, a filter 128, and a controller 118. Pneumatic pump 120 can be fluidly coupled to removed fluid canister 106 (e.g., via conduit 136) and can be configured to draw a vacuum within canister 106 by pumping air out of canister 106. In some embodiments, pneumatic pump 120 is configured to operate in both a forward direction and a reverse direction. For example, pneumatic pump 120 can operate in the forward direction to pump air out of canister 106 and decrease the pressure within canister 106. Pneumatic pump 120 can operate in the reverse direction to pump air into canister 106 and increase the pressure within canister 106. Pneumatic pump 120 can be controlled by controller 118, described in greater detail below.

Similarly, instillation pump 122 can be fluidly coupled to instillation fluid canister 104 via tubing 109 and fluidly coupled to wound dressing 112 via tubing 108. Instillation pump 122 can be operated to deliver instillation fluid 105 to wound dressing 112 and wound 114 by pumping instillation fluid 105 through tubing 109 and tubing 108, as shown in FIG. 4. Instillation pump 122 can be controlled by controller 118, described in greater detail below.

Filter 128 can be positioned between removed fluid canister 106 and pneumatic pump 120 (e.g., along conduit 136) such that the air pumped out of canister 106 passes through filter 128. Filter 128 can be configured to prevent liquid or solid particles from entering conduit 136 and reaching pneumatic pump 120. Filter 128 may include, for example, a bacterial filter that is hydrophobic and/or lipophilic such that aqueous and/or oily liquids will bead on the surface of filter 128. Pneumatic pump 120 can be configured to provide sufficient airflow through filter 128 that the pressure drop across filter 128 is not substantial (e.g., such that the pressure drop will not substantially interfere with the application of negative pressure to wound 114 from therapy device 102).

In some embodiments, therapy device 102 operates a valve 132 to controllably vent the negative pressure circuit, as shown in FIG. 3A. Valve 132 can be fluidly connected with pneumatic pump 120 and filter 128 via conduit 136. In some embodiments, valve 132 is configured to control airflow between conduit 136 and the environment around therapy device 102. For example, valve 132 can be opened to allow airflow into conduit 136 via vent 134 and conduit 138, and closed to prevent airflow into conduit 136 via vent 134 and conduit 138. Valve 132 can be opened and closed by controller 118, described in greater detail below. When valve 132 is closed, pneumatic pump 120 can draw a vacuum within a negative pressure circuit by causing airflow through filter 128 in a first direction, as shown in FIG. 2. The negative pressure circuit may include any component of system 100 that can be maintained at a negative pressure when performing negative pressure wound therapy (e.g., conduit 136, removed fluid canister 106, tubing 110, wound dressing 112, and/or wound 114). For example, the negative pressure circuit may include conduit 136, removed fluid canister 106, tubing 110, wound dressing 112, and/or wound 114. When valve 132 is open, airflow from the environment around therapy device 102 may enter conduit 136 via vent 134 and conduit 138 and fill the vacuum within the negative pressure circuit. The airflow from conduit 136 into canister 106 and other volumes within the negative pressure circuit may pass through filter 128 in a second direction, opposite the first direction, as shown in FIG. 3A.

In some embodiments, therapy device 102 vents the negative pressure circuit via an orifice 158, as shown in FIG. 3B. Orifice 158 may be a small opening in conduit 136 or any other component of the negative pressure circuit (e.g., removed fluid canister 106, tubing 110, tubing 111, wound dressing 112, etc.) and may allow air to leak into the negative pressure circuit at a known rate. In some embodiments, therapy device 102 vents the negative pressure circuit via orifice 158 rather than operating valve 132. Valve 132 can be omitted from therapy device 102 for any embodiment in which orifice 158 is included. The rate at which air leaks into the negative pressure circuit via orifice 158 may be substantially constant or may vary as a function of the negative pressure, depending on the geometry of orifice 158. For embodiments in which the leak rate via orifice 158 is variable, controller 118 can use a stored relationship between negative pressure and leak rate to calculate the leak rate via orifice 158 based measurements of the negative pressure. Regardless of whether the leak rate via orifice 158 is substantially constant or variable, the leakage of air into the negative pressure circuit via orifice 158 can be used to generate a pressure decay curve for use in estimating the volume of wound 114, as described with reference to FIGS. 5-9.

In some embodiments, therapy device 102 includes a variety of sensors. For example, therapy device 102 is shown to include a pressure sensor 130 configured to measure the pressure within canister 106 and/or the pressure at wound dressing 112 or wound 114. In some embodiments, therapy device 102 includes a pressure sensor 113 configured to measure the pressure within tubing 111. Tubing 111 may be connected to wound dressing 112 and may be dedicated to measuring the pressure at wound dressing 112 or wound 114 without having a secondary function such as channeling installation fluid 105 or wound exudate. In various embodiments, tubing 108, 110, and 111 may be physically separate tubes or separate lumens within a single tube that connects therapy device 102 to wound dressing 112. Accordingly, tubing 110 may be described as a negative pressure lumen that functions apply negative pressure wound dressing 112 or wound 114, whereas tubing 111 may be described as a sensing lumen configured to sense the pressure at wound dressing 112 or wound 114. Pressure sensors 130 and 113 can be located within therapy device 102, positioned at any location along tubing 108, 110, and 111, or located at wound dressing 112 in various embodiments. Pressure measurements recorded by pressure sensors 130 and/or 113 can be communicated to controller 118. Controller 118 use the pressure measurements as inputs to various pressure testing operations and control operations performed by controller 118 (described in greater detail with reference to FIGS. 5-12).

Controller 118 can be configured to operate pneumatic pump 120, instillation pump 122, valve 132, and/or other controllable components of therapy device 102. In some embodiments, controller 118 performs a pressure testing procedure by applying a pressure stimulus to the negative pressure circuit. For example, controller 118 may instruct valve 132 to close and operate pneumatic pump 120 to establish negative pressure within the negative pressure circuit. Once the negative pressure has been established, controller 118 may deactivate pneumatic pump 120. Controller 118 may cause valve 132 to open for a predetermined amount of time and then close after the predetermined amount of time has elapsed. Controller 118 may observe a dynamic pressure response of the negative pressure circuit to the pressure stimulus using pressure measurements recorded by pressure sensors 130 and/or 113. The dynamic pressure response may be characterized by a variety of parameters including, for example, a depth of purge parameter, a rebound parameter, a delta parameter, and a leak rate parameter (described in greater detail with reference to FIG. 5).

Controller 118 can estimate the volume of wound 114 based on the observed dynamic pressure response. For example, controller 118 can apply the observed parameters as inputs to a pressure model that defines a relationship between the observed parameters and the volume of the negative pressure circuit and/or the volume of wound 114. The model may include a polynomial approximation model, a neural network model, or any other model that relates the observed parameters to the volume of the negative pressure circuit and/or the volume of wound 114. In some embodiments, the pressure model is a pre-existing model stored in controller 118 by the manufacturer of therapy device 102. In other embodiments, controller 118 can generate the pressure model on-site by performing a training procedure.

The training procedure may be the same as the pressure testing procedure with the exception that therapy device 102 is connected to a training circuit having a known volume. For example, wound dressing 112 can be applied to a test device having a known volume rather than to a patient's skin 116 surrounding wound 114. Controller 118 can apply the pressure stimulus to various training circuits having various known volumes and may observe the dynamic pressure response of each training circuit. Each of the known volumes may result in a different dynamic pressure response to the pressure stimulus. Controller 118 can then associate the known volume of each training circuit with the corresponding dynamic pressure response. In some embodiments, controller 118 uses the dynamic pressure responses of the training circuits to generate the pressure model that defines a relationship between the observed parameters of the dynamic pressure response (e.g., depth of purge, rebound, delta, leak rate, etc.) and the volume of the training circuit. The pressure model can then be stored in controller 118 and used to estimate the volume of a wound 114, as previously described.

In some embodiments, controller 118 is configured to execute the pressure testing procedure, observe the dynamic pressure response, and estimate the wound volume at a plurality of times during wound treatment. Controller 118 can then determine healing progression based on changes in the wound volume during wound treatment. In some embodiments, controller 118 is configured to determine a volume of instillation fluid 105 to deliver to wound 114 based on the estimated wound volume. The volume of instillation fluid 105 to deliver may be a predetermined percentage of the volume of wound 114 (e.g., 20%, 50%, 80%, etc.). Controller 118 can then operate instillation pump 122 to deliver the determined volume of instillation fluid 105 to wound 114. These and other features of controller 118 are described in greater detail with reference to FIGS. 5-12.

In some embodiments, therapy device 102 includes a user interface 126. User interface 126 may include one or more buttons, dials, sliders, keys, or other input devices configured to receive input from a user. User interface 126 may also include one or more display devices (e.g., LEDs, LCD displays, etc.), speakers, tactile feedback devices, or other output devices configured to provide information to a user. In some embodiments, the pressure measurements recorded by pressure sensors 130 and/or 113 are presented to a user via user interface 126. User interface 126 can also display alerts generated by controller 118. For example, controller 118 can generate a "no canister" alert if canister 106 is not detected.

In some embodiments, therapy device 102 includes a data communications interface 124 (e.g., a USB port, a wireless transceiver, etc.) configured to receive and transmit data. Communications interface 124 may include wired or wireless communications interfaces (e.g., jacks, antennas, transmitters, receivers, transceivers, wire terminals, etc.) for conducting data communications external systems or devices. In various embodiments, the communications may be direct (e.g., local wired or wireless communications) or via a communications network (e.g., a WAN, the Internet, a cellular network, etc.). For example, communications interface 124 can include a USB port or an Ethernet card and port for sending and receiving data via an Ethernet-based communications link or network. In another example, communications interface 124 can include a Wi-Fi transceiver for communicating via a wireless communications network or cellular or mobile phone communications transceivers. Controller Referring now to FIG. 5, a block diagram illustrating controller 118 in greater detail is shown, according to an exemplary embodiment. Controller 118 is shown to include a processing circuit 140 including a processor 142 and memory 144. Processor 142 may be a general purpose or specific purpose processor, an application specific integrated circuit (ASIC), one or more field programmable gate arrays (FPGAs), a group of processing components, or other suitable processing components. Processor 142 is configured to execute computer code or instructions stored in memory 144 or received from other computer readable media (e.g., CDROM, network storage, a remote server, etc.).

Memory 144 may include one or more devices (e.g., memory units, memory devices, storage devices, etc.) for storing data and/or computer code for completing and/or facilitating the various processes described in the present disclosure. Memory 144 may include random access memory (RAM), read-only memory (ROM), hard drive storage, temporary storage, non-volatile memory, flash memory, optical memory, or any other suitable memory for storing software objects and/or computer instructions. Memory 144 may include database components, object code components, script components, or any other type of information structure for supporting the various activities and information structures described in the present disclosure. Memory 144 may be communicably connected to processor 142 via processing circuit 140 and may include computer code for executing (e.g., by processor 142) one or more processes described herein. When processor 142 executes instructions stored in memory 144, processor 142 generally configures controller 118 (and more particularly processing circuit 140) to complete such activities.

Controller 118 is shown to include a pump controller 146 and a valve controller 150. Pump controller 146 can be configured to operate pumps 120 and 122 by generating and providing control signals to pumps 120-122. The control signals provided to pumps 120-122 can cause pumps 120-122 to activate, deactivate, or achieve a variable capacity or speed (e.g., operate at half speed, operate at full speed, etc.). Similarly, valve controller 150 can be configured to operate valve 132 by generating and providing control signals to valve 132. The control signals provided to valve 132 can cause valve 132 to open, close, or achieve a specified intermediate position (e.g., one-third open, half open, etc.). In some embodiments, pump controller 146 and valve controller 150 are used by other components of controller 118 (e.g., testing procedure controller 148, wound volume estimator 156, etc.) to operate pumps 120-122 and valve 132 when carrying out the processes described herein.

In some embodiments, pump controller 146 uses input from a canister sensor configured to detect whether removed fluid canister 106 is present. Pump controller 146 can be configured to activate pneumatic pump 120 only when removed fluid canister 106 is present. For example, pump controller 146 can check whether canister 106 is present and can activate pneumatic pump 120 in response to a determination that canister 106 is present. However, if canister 106 is not present, pump controller 146 may prevent pneumatic pump 120 from activating. Similarly, pump controller 146 can be configured to activate instillation pump 122 only when instillation fluid canister 104 is present. For example, pump controller 146 can check whether canister 104 is present and can activate instillation pump 122 in response to a determination that canister 104 is present. However, if canister 104 is not present, pump controller 146 may prevent instillation pump 122 from activating.

Controller 118 is shown to include a pressure monitor 152. Pressure monitor 152 can be configured to monitor the pressure within removed fluid canister 106 and/or the pressure within wound dressing 112 or wound 114 using feedback from pressure sensors 130 and/or 113. For example, pressure sensors 130 and/or 113 may provide pressure measurements to pressure monitor 152. Pressure monitor 152 can use the pressure measurements to determine the pressure within canister 106 and/or the pressure within wound dressing 112 or wound 114 in real-time. Pressure monitor 152 can provide the pressure value to model generator 154, pump controller 146, testing procedure controller 148, and/or valve controller 150 for use as an input to control processes performed by such components.

Referring now to FIGS. 5 and 6A-6C, controller 118 is shown to include a testing procedure controller 148. Testing procedure controller 148 can be configured to execute a pressure testing procedure to invoke and observe a dynamic pressure response. If therapy device 102 is connected to a wound dressing 112 applied to a patient's skin 116 over a wound 114, testing procedure controller 148 can observe the dynamic pressure response of a negative pressure circuit that includes conduit 136, removed fluid canister 106, tubing 110, wound dressing 112, and/or wound 114 (which may have an unknown volume). If therapy device 102 is connected to a wound dressing 112 applied to a training device having a known volume, testing procedure controller 148 can observe the dynamic pressure response of a training circuit that includes conduit 136, removed fluid canister 106, tubing 110, wound dressing 112, and/or the training device.

Figure 6A:
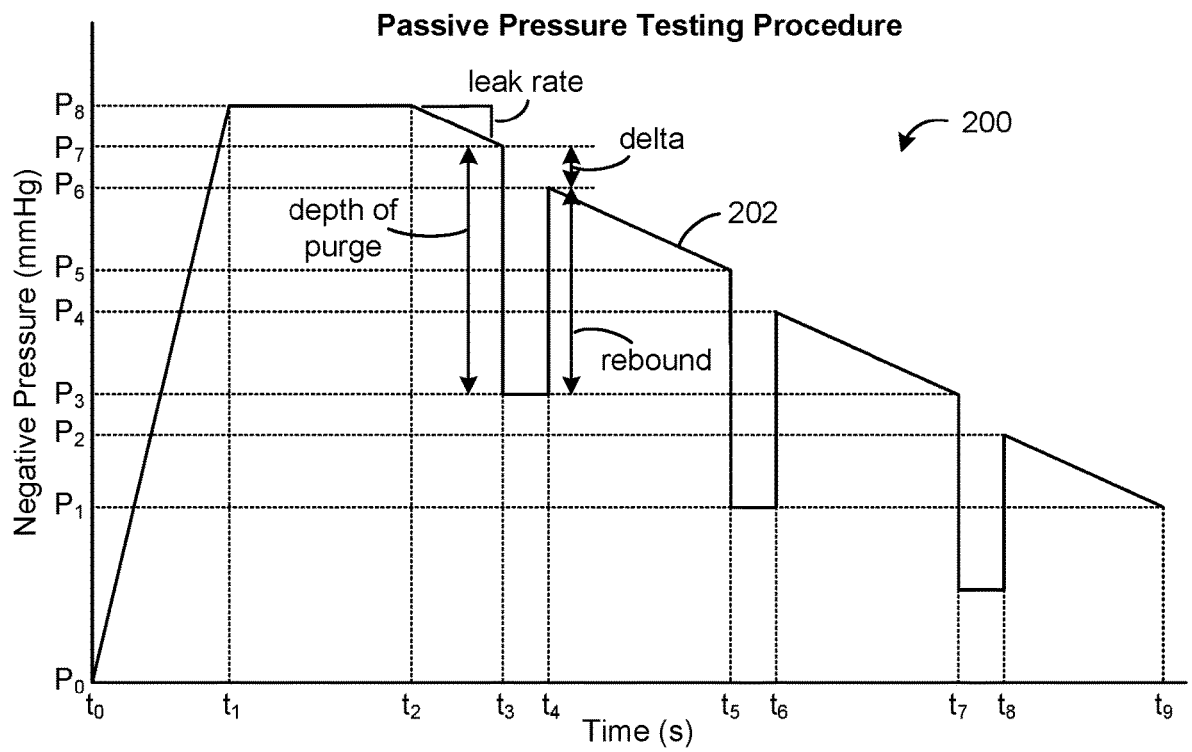
FIG. 6A is a graph illustrating a passive pressure testing procedure which can be performed by the therapy device of FIG. 1, according to an exemplary embodiment.

Referring particularly to FIG. 6A, a graph 200 illustrating a passive pressure testing procedure performed by testing procedure controller 148 is shown, according to an exemplary embodiment. Testing procedure controller 148 can be configured to operate pneumatic pump 120 to establish negative pressure within the negative pressure circuit and/or the training circuit.

The negative pressure may be defined as the difference between the atmospheric pressure surrounding therapy device 102 and the pressure within the negative pressure circuit and/or the training circuit (i.e., the amount by which atmospheric pressure exceeds the pressure within the negative pressure circuit and/or the training circuit). For example, at time $t_0$, the negative pressure is shown having a value of $P_0$ (e.g., zero mmHg), which indicates that the pressure within the negative pressure circuit and/or the training circuit is equal to atmospheric pressure around therapy device 102.

At time $t_0$, testing procedure controller 148 begins operating pneumatic pump 120 to reduce the pressure within the negative pressure circuit and/or the training circuit. The negative pressure continues to decrease until it reaches a negative pressure value of $P_8$ mmHg below atmospheric pressure (e.g., 125 mmHg) at time $t_1$. Between time $t_1$ and time $t_2$, testing procedure controller 148 maintains the negative pressure at the value of $P_8$ by operating pneumatic pump 120 as needed to remove air from the negative pressure circuit and/or the training circuit. Testing procedure controller 148 may then apply a pressure stimulus to the negative pressure circuit and/or the training circuit after the negative pressure has been established within the negative pressure circuit and/or the training circuit.

At time $t_2$, testing procedure controller 148 deactivates pneumatic pump 120. Beginning at time $t_2$, the magnitude of the negative pressure within the negative pressure circuit and/or the training circuit may decrease due to leakage of air into the negative pressure circuit and/or the training circuit while valve 132 is closed. The rate at which the negative pressure decreases while valve 132 is closed is defined by the slope of line 202 between time $t_2$ and time $t_3$. Testing procedure controller 148 may determine the slope of line 202 between time $t_2$ and time $t_3$ and may store the slope as the value of the leak rate parameter. The leak rate parameter may be one of the parameters that characterizes the dynamic pressure response of the negative pressure circuit and/or the training circuit.

At time $t_3$, testing procedure controller 148 applies a pressure stimulus to the negative pressure circuit and/or the training circuit. Applying the pressure stimulus may include operating valve 132 to controllably vent the negative pressure circuit and/or the training circuit. For example, testing procedure controller 148 may cause valve 132 to open at time $t_3$ to allow airflow into the negative pressure circuit and/or the training circuit. Testing procedure controller 148 may keep valve 132 open for a predetermined amount of time (i.e., from time $t_3$ to time $t_4$) and may close valve 132 after closing the valve after the predetermined amount of time has elapsed (i.e., at time $t_4$).

At time $t_4$, testing procedure controller 148 may observe the dynamic pressure response of the negative pressure circuit and/or the training circuit to the pressure stimulus. The dynamic pressure response may be characterized by several additional parameters including a depth of purge parameter, a rebound parameter, and a delta parameter. The depth of purge parameter may be defined as the difference between a measured value of the negative pressure $P_7$ before valve 132 is opened and a measured value of the negative pressure $P_3$ while valve 132 is open (i.e., depth of purge=$P_7$−$P_3$). The rebound parameter may be defined as the difference between a measured value of the negative pressure $P_6$ after valve 132 is closed and a measured value of the negative pressure $P_3$ while valve 132 is open (i.e., rebound=$P_6$−$P_3$). The delta parameter may be defined as the difference between a measured value of the negative pressure $P_7$ before valve 132 is opened and a measured value of the negative pressure $P_6$ after valve 132 is closed (i.e., delta=$P_7$−$P_6$).

In some embodiments, testing procedure controller 148 applies the pressure stimulus one or more additional times until the negative pressure reaches a threshold value $P_1$ when valve 132 is closed. Between each application of the pressure stimulus, testing procedure controller 148 may wait for another predetermined amount of time (i.e., from time $t_4$ to time $t_5$ and from time $t_6$ to time $t_7$). For example, testing procedure controller 148 may wait for a predetermined amount of time from time $t_4$ to time $t_5$ and may apply the pressure stimulus again at time $t_5$. Testing procedure controller 148 may cause valve 132 to open at time $t_5$ to allow airflow into the negative pressure circuit and/or the training circuit. Testing procedure controller 148 may keep valve 132 open for a predetermined amount of time (i.e., from time $t_5$ to time $t_6$) and may close valve 132 after closing the valve after the predetermined amount of time has elapsed (i.e., at time $t_6$). At time $t_6$, testing procedure controller 148 may record values of the depth of purge parameter (i.e., depth of purge=$P_5$−$P_1$), the rebound parameter (i.e., rebound=$P_4$−$P_1$), and the delta parameter (i.e., delta=$P_5$−$P_4$) in response to the second application of the pressure stimulus. This process can be repeated until the value of the negative pressure within the negative pressure circuit and/or the training circuit reaches the threshold pressure value $P_1$ at time $t_9$.

Figure 6B:
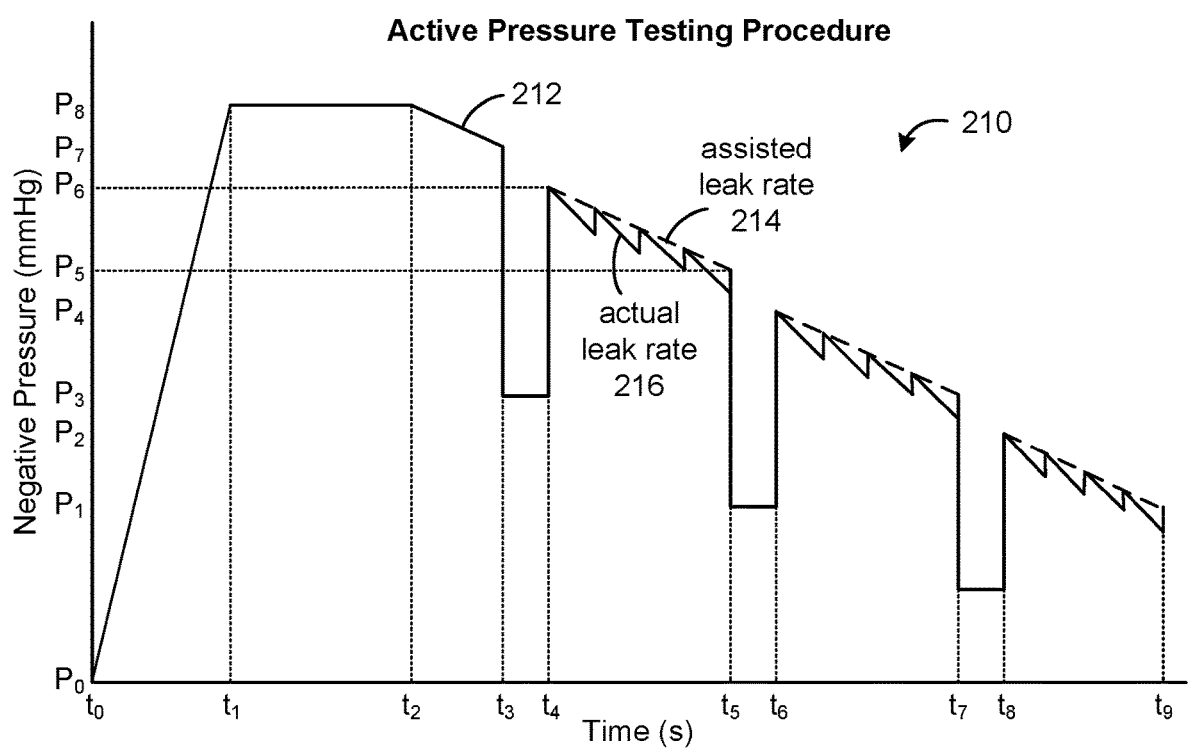
FIG. 6B is a graph illustrating an active pressure testing procedure which can be performed by the therapy device of FIG. 1, according to an exemplary embodiment.

Referring particularly to FIG. 6B, a graph 210 illustrating an active testing procedure performed by testing procedure controller 148 is shown, according to an exemplary embodiment. Testing procedure controller 148 can be configured to operate pneumatic pump 120 to establish negative pressure within the negative pressure circuit and/or the training circuit. The negative pressure may be defined as the difference between the atmospheric pressure surrounding therapy device 102 and the pressure within the negative pressure circuit and/or the training circuit (i.e., the amount by which atmospheric pressure exceeds the pressure within the negative pressure circuit and/or the training circuit). For example, at time $t_0$, the negative pressure is shown having a value of $P_0$ (e.g., zero mmHg), which indicates that the pressure within the negative pressure circuit and/or the training circuit is equal to atmospheric pressure around therapy device 102.

The active testing procedure illustrated in FIG. 6B may be substantially similar to the passive testing procedure illustrated in FIG. 6A. However, in the active testing procedure, controller 148 can be configured to operate pneumatic pump 120 using brief controlled activations of pneumatic pump 120 while valve 132 is closed (e.g., between times $t_4$ and $t_5$, between times $t_6$ and $t_7$, and between times $t_8$ and $t_9$) to compensate for a high leak rate of air into the negative pressure circuit and/or the training circuit. In graph 210, line 212 represents the pressure within the negative pressure circuit and/or the training circuit as a function of time. The actual leak rate of air into the negative pressure circuit and/or the training circuit while valve 132 is closed is indicated by the slope of line segments 216, whereas the slope of line 214 represents the average or assisted leak rate between times $t_4$ and $t_5$. The brief controlled activations of pneumatic pump 120 remove some of the air from the negative pressure circuit and/or the training circuit between times $t_4$ and $t_5$ (causing the negative pressure to increase with each controlled activation) such that the average or assisted leak rate is equal to $$\frac{P_6 - P_5}{t_5 - t_4}.$$

Similar negative pressure adjustments can be made between times $t_6$ and $t_7$ and between times $t_8$ and $t_9$. In this way, the influx of air into the negative pressure circuit and/or training can be mitigated to compensate for a high actual leak rate while valve 132 is closed.

Figure 6C:
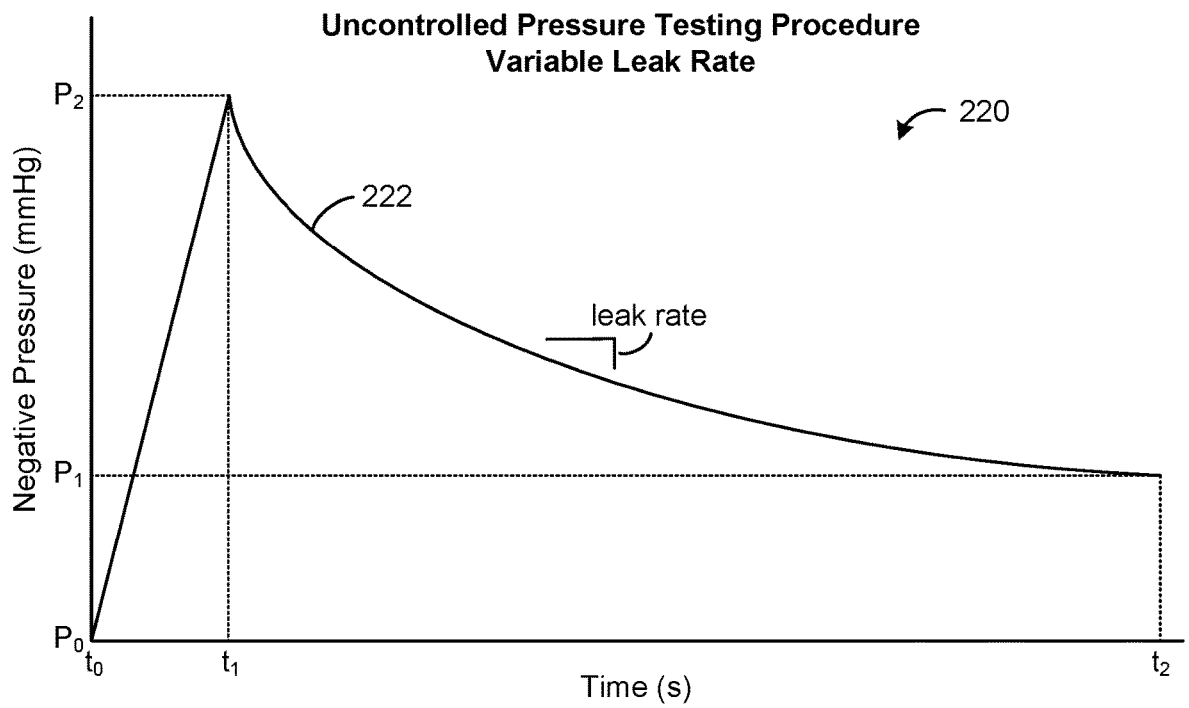
FIG. 6C is a graph illustrating an uncontrolled pressure testing procedure with a variable leak rate which can be performed by the therapy device of FIG. 1, according to an exemplary embodiment.
Figure 6D:
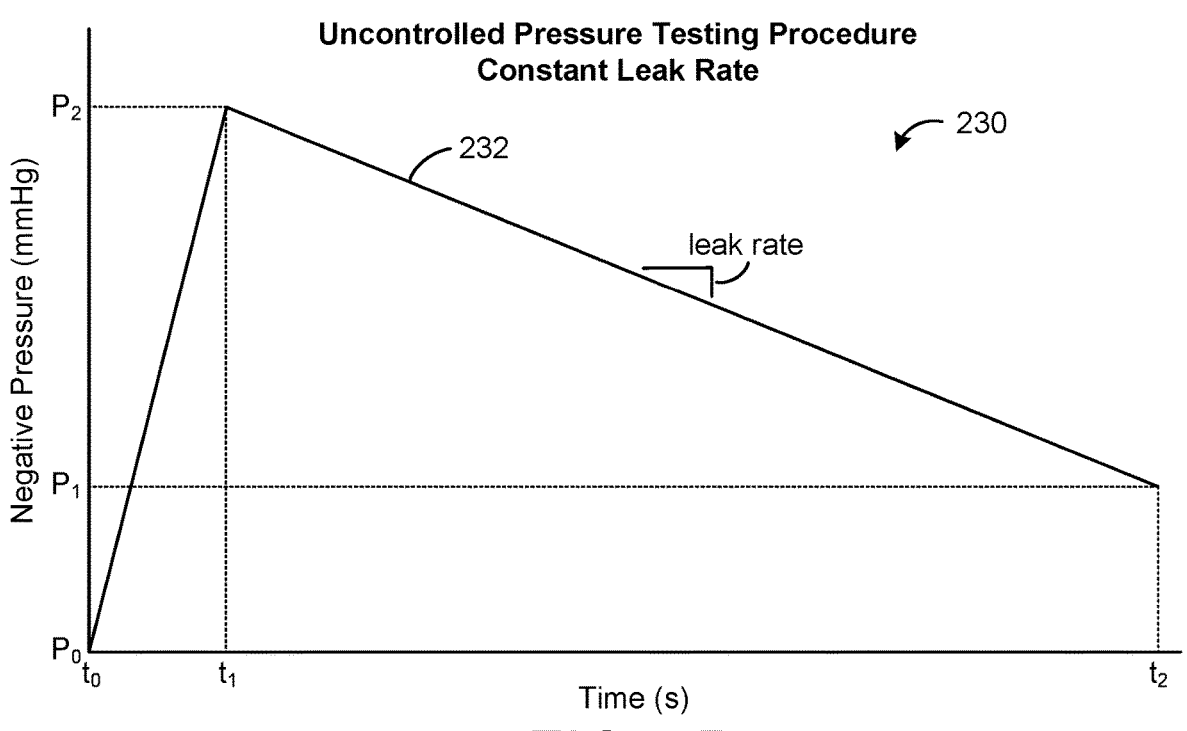
FIG. 6D is a graph illustrating an uncontrolled pressure testing procedure with a constant leak rate which can be performed by the therapy device of FIG. 1, according to an exemplary embodiment.

Referring particularly to FIGS. 6C-6D, graphs 220 and 230 illustrating an uncontrolled testing procedure performed by testing procedure controller 148 is shown, according to an exemplary embodiment. Unlike the passive testing procedure and active testing procedure described with reference to FIGS. 6A and 6B, the uncontrolled testing procedure does not make use of valve 132 and can be performed for embodiments in which therapy device 102 includes orifice 158 in place of valve 132. Graph 220 illustrates the uncontrolled testing procedure when orifice 158 leaks air into the negative pressure circuit and/or training circuit at a variable leak rate, whereas graph 220 illustrates the uncontrolled testing procedure when orifice 158 leaks air into the negative pressure circuit and/or training circuit at a substantially constant leak rate.

In both uncontrolled testing procedures, at time $t_0$, testing procedure controller 148 begins operating pneumatic pump 120 to reduce the pressure within the negative pressure circuit and/or the training circuit. The negative pressure continues to decrease until it reaches a negative pressure value of $P_2$ mmHg below atmospheric pressure (e.g., 125 mmHg) at time $t_1$.

At time $t_1$, testing procedure controller 148 deactivates pneumatic pump 120. Beginning at time $t_1$, the magnitude of the negative pressure within the negative pressure circuit and/or the training circuit may decrease due to leakage of air into the negative pressure circuit and/or the training circuit via orifice 158. The rate at which the negative pressure decreases is defined by the slope of line 222 between time $t_1$ and time $t_2$. In graph 220, leakage of air into the negative pressure circuit and/or training circuit via orifice 158 occurs more quickly near time $t_1$ and more slowly near time $t_2$, as shown by the slope of line 222 becoming closer to zero as time elapses between $t_1$ and $t_2$. In graph 230, leakage of air into the negative pressure circuit and/or training circuit via orifice 158 occurs at a substantially constant rate, as shown by the substantially linear line 232. In either scenario, testing procedure controller 148 may determine the slope of line 222 at one or more times between time $t_1$ and time $t_2$ and may store the slope as the value of the leak rate parameter. Alternatively, the leak rate parameter can be defined as the amount of time required for the negative pressure to drop from $P_2$ to $P_1$ and can be calculated by subtracting $t_1$ from $t_2$ (i.e., $t_2-t_1$). The leak rate parameter may be one of the parameters that characterizes the dynamic pressure response of the negative pressure circuit and/or the training circuit.

Testing procedure controller 148 can be configured to execute the passive testing procedure, the active testing procedure, and/or the uncontrolled testing procedure in various embodiments. The passive testing procedure may be suitable under most conditions and may be the primary or default testing procedure used by testing procedure controller 148. However, the active testing procedure may be suitable in the presence of a high leak rate and may be used by testing procedure controller 148 in response to a determination that the actual leak rate exceeds a predetermined leak rate threshold. The uncontrolled testing procedure may be suitable for embodiments in which valve 132 is replaced with orifice 158.

Leak rate can be determined in a variety of ways. In some embodiments, leak rate is determined by operating pneumatic pump 120 to achieve a predetermined negative pressure within the negative pressure circuit and measuring the pressure decay over time. In some embodiments, leak rate is determined based on the effort of pneumatic pump 120 or power consumed by pneumatic pump 120. For example, pump controller 146 can be configured to perform brief controlled activations of pneumatic pump 120 to maintain the negative pressure at a setpoint or prevent the negative pressure from dropping at a rate that exceeds a predetermined leak rate threshold, as previously described. The number or frequency of these brief controlled activations of pneumatic pump 120 depends on the leak rate and can be used to determine the leak rate. Similarly, the power consumed by pneumatic pump 120 to perform these brief controlled activations depends on the leak rate and can be used to determine the leak rate. For example, controller 118 can be configured to record the number of brief controlled activations of pneumatic pump 120 within a given time period, measure a frequency or interval of the brief controlled activations, measure a duty cycle of pneumatic pump 120 (e.g., a percentage of time pneumatic pump 120 is active), or measure an amount of power consumed by pneumatic pump 120 to perform the brief controlled activations. Any of these metrics may characterize pump effort and can be stored as a pump effort parameter. Controller 118 can use a stored equation or predetermined relationship to calculate leak rate as a function of the pump effort.

Referring again to FIG. 5, controller 118 is shown to include a model generator 154. Model generator 154 can be configured to generate a model that defines a relationship between the parameters of the dynamic pressure response and the volume of wound 114. To generate the model, model generator 154 can cause testing procedure controller 148 to run the pressure testing procedure outlined above for several different training circuits having several different known volumes (e.g., 50 cc, 100 cc, 200 cc, 300 cc, etc.). When the pressure testing procedure is performed on a training circuit having a known volume, the pressure testing procedure may be referred to as a training procedure. Each performance of the training procedure may include applying the pressure stimulus to a training circuit having a known volume, observing the dynamic pressure response of the training circuit to the pressure stimulus, and associating the known volume with the dynamic pressure response of the training circuit.

In some embodiments, model generator 154 records the values of the parameters of the dynamic pressure response (i.e., leak rate, depth of purge, rebound, delta, etc.) for each known volume and associates those values with the known volume. The values of the parameters and the known volume form a set of training data which can be used to construct a model. The values of the parameters form a set of model input training data, whereas the known volumes form a set of model output training data. Model generator 154 can use any of a variety of model generation techniques to construct a model (i.e., a mathematical model) that relates the values of the parameters to the corresponding volume in the set of training data.

In some embodiments, model generator 154 creates a polynomial approximation model to relate the values of the parameters to the corresponding volume. To generate a polynomial approximation model, model generator 154 can perform a curve fitting process such as polynomial regression using any of a variety of regression techniques. Examples of regression techniques which can be used by model generator 154 include least squares, ordinary least squares, linear least squares, partial least squares, total least squares, generalized least squares, weighted least squares non-linear least squares, non-negative least squares, iteratively reweighted least squares, ridge regression, least absolute deviations, Bayesian linear regression, Bayesian multivariate linear regression, etc.

In other embodiments, model generator 154 creates a neural network model to relate the values of the parameters to the corresponding volume. To generate a neural network model, model generator 154 can perform a machine learning process. Examples of machine learning techniques which can be used by model generator 154 include decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning, etc.

Figure 7A:
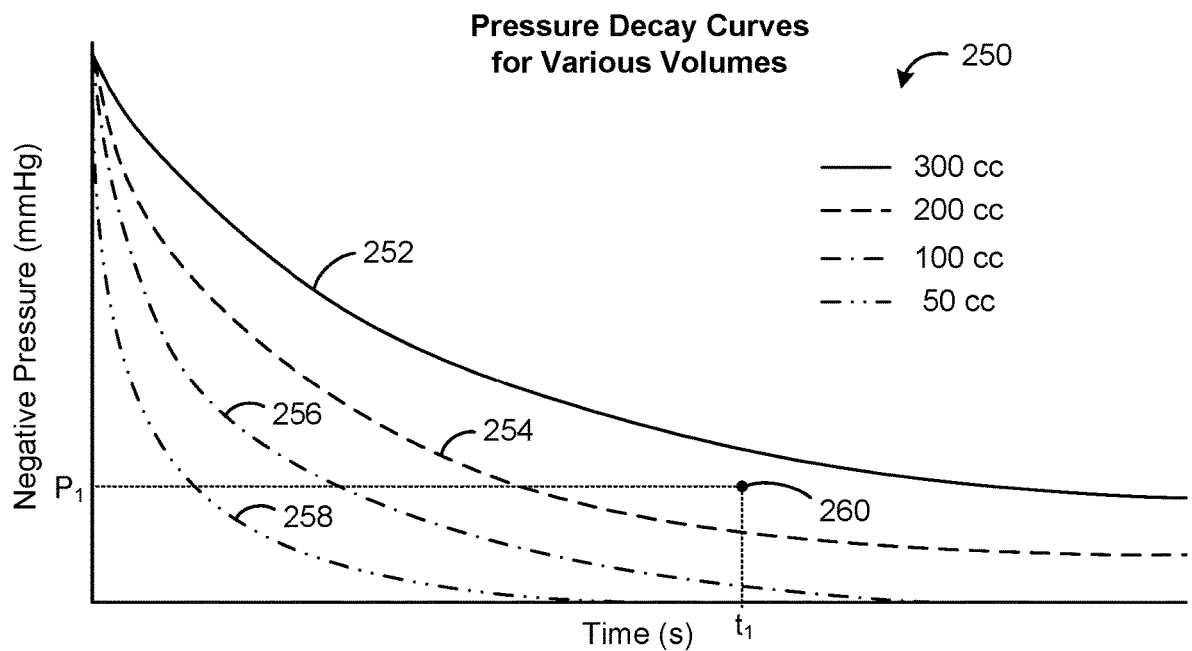
FIG. 7A is a graph illustrating several pressure decay curves which can be generated and/or used by the therapy device of FIG. 1 to relate measured pressure to wound volume, according to an exemplary embodiment.

Referring now to FIG. 7A, a graph 250 illustrating several pressure decay curves 252, 254, 256, and 258 are shown, according to an exemplary embodiment. Each of pressure decay curves 252-258 corresponds to a known volume and represents the pressure within the negative pressure circuit and/or the training circuit as a function of time for the corresponding volume. For example, pressure decay curve 252 corresponds to a volume of 300 cc, pressure decay curve 254 corresponds to a volume of 200 cc, pressure decay curve 256 corresponds to a volume of 100 cc, pressure decay curve 258 corresponds to a volume of 50 cc. Each of pressure decay curves 252-258 may be created by model generator 154 using any of the modeling techniques described above. For example, pressure decay curves 252-258 can be created by running the pressure testing procedure for each known volume and plotting the pressure decay over time for each known volume.

In some embodiments, controller 118 uses pressure decay curves 252-258 to translate a measured pressure value into a corresponding volume when estimating the volume of wound 114. For example, controller 118 can measure the pressure of the negative pressure circuit and identify a time at which the pressure was measured. Controller 118 can interpolate between pressure decay curves 252-258 to determine an interpolated pressure value that corresponds to the measured pressure and time pair. For example, at time $t_1$, controller 118 may observe a pressure value of $P_1$. The combination of time $t_1$ and pressure $P_1$ defines a point 260 in graph 250. Point 260 lies approximately halfway between pressure decay curve 252 and pressure decay curve 254. Controller 118 can interpolate between pressure decay curves 252 and 254 to estimate that the volume of the negative pressure circuit is approximately halfway between the known volumes corresponding to pressure decay curves 252 and 254 (i.e., approximately 250 cc). In other embodiments, controller 118 estimates the volume of wound 114 by applying observed parameters of a dynamic pressure response as inputs to a pressure model.

Figure 7B:
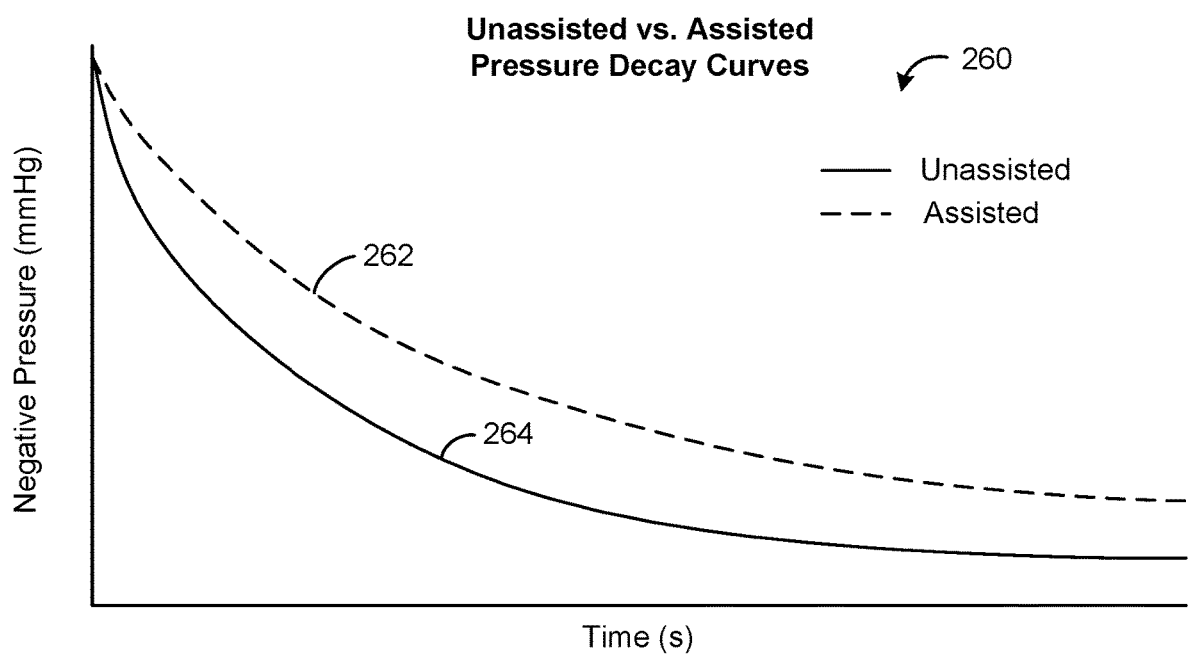
FIG. 7B is a graph illustrating an unassisted pressure decay curve generated using the passive pressure testing procedure of FIG. 6A and an assisted pressure decay curve generated using the active pressure testing procedure of FIG. 6B, according to an exemplary embodiment.

Referring now to FIG. 7B, a graph 260 illustrating an unassisted pressure decay curve 264 and an assisted pressure decay curve 262 is shown, according to an exemplary embodiment. In graph 260, both unassisted pressure decay curve 264 and assisted pressure decay curve 262 correspond to the same volume of the negative pressure circuit and/or training circuit. Unassisted pressure decay curve 264 illustrates the pressure decay during the passive testing procedure shown in FIG. 6A (i.e., when pneumatic pump 120 is not operated to compensate for a high leak rate). Conversely, assisted pressure decay curve 262 illustrates the pressure decay during the active testing procedure (i.e., when pneumatic pump 120 is operated to compensate for a high leak rate). As discussed with reference to FIG. 6B, operating pneumatic pump 120 during the active testing procedure mitigates the pressure decay and therefore results in a more gradual assisted pressure decay curve 262 relative to unassisted pressure decay curve 264.

Referring again to FIG. 5, controller 118 is shown to include a wound volume estimator 156. Wound volume estimator 156 can be configured to estimate the volume of wound 114 based on pressure measurements collected by pressure sensors 130 and/or 113. In some embodiments, wound volume estimator 156 estimates the volume of wound 114 by performing a pressure testing procedure. The pressure testing procedure may include applying a pressure stimulus to the negative pressure circuit and observing the dynamic pressure response of the negative pressure circuit to the pressure stimulus. As described above, the negative pressure circuit may include any component of system 100 that can be maintained at a negative pressure when performing negative pressure wound therapy (e.g., conduit 136, removed fluid canister 106, tubing 110, wound dressing 112, and/or wound 114).

To perform the pressure testing procedure, wound volume estimator 156 may instruct valve 132 to close and operate pneumatic pump 120 to establish negative pressure within the negative pressure circuit. Once the negative pressure has been established, wound volume estimator 156 may deactivate pneumatic pump 120. Wound volume estimator 156 may cause valve 132 to open for a predetermined amount of time and then close after the predetermined amount of time has elapsed. Wound volume estimator 156 may observe a dynamic pressure response of the negative pressure circuit to the pressure stimulus using pressure measurements recorded by pressure sensors 130 and/or 113. The dynamic pressure response may be characterized by a variety of parameters including, for example, a depth of purge parameter, a rebound parameter, a delta parameter, and a leak rate parameter, as previously described.

Wound volume estimator 156 can estimate the volume of wound 114 based on the observed dynamic pressure response. For example, wound volume estimator 156 can apply the observed parameters as inputs to a pressure model that defines a relationship between the observed parameters and the volume of the negative pressure circuit and/or the volume of wound 114. In some embodiments, the pressure model is the model created by model generator 154 (e.g., by performing the training procedure based on training data collected using the training circuits). The model may include a polynomial approximation model, a neural network model, or any other model that relates the observed parameters to the volume of the negative pressure circuit and/or the volume of wound 114. In other embodiments, the pressure model is a pre-existing model stored in memory 144 by the manufacturer of therapy device 102.

In some embodiments, wound volume estimator 156 is configured to execute the pressure testing procedure, observe the dynamic pressure response, and estimate the wound volume at a plurality of times during wound treatment. Wound volume estimator 156 can then determine healing progression based on changes in the wound volume during wound treatment. In some embodiments, wound volume estimator 156 is configured to determine a volume of instillation fluid 105 to deliver to wound 114 based on the estimated wound volume. The volume of instillation fluid 105 to deliver may be a predetermined percentage of the volume of wound 114 (e.g., 20%, 50%, 80%, etc.). Wound volume estimator 156 can then operate instillation pump 122 to deliver the determined volume of instillation fluid 105 to wound 114.

Flow Diagrams

Figure 8:
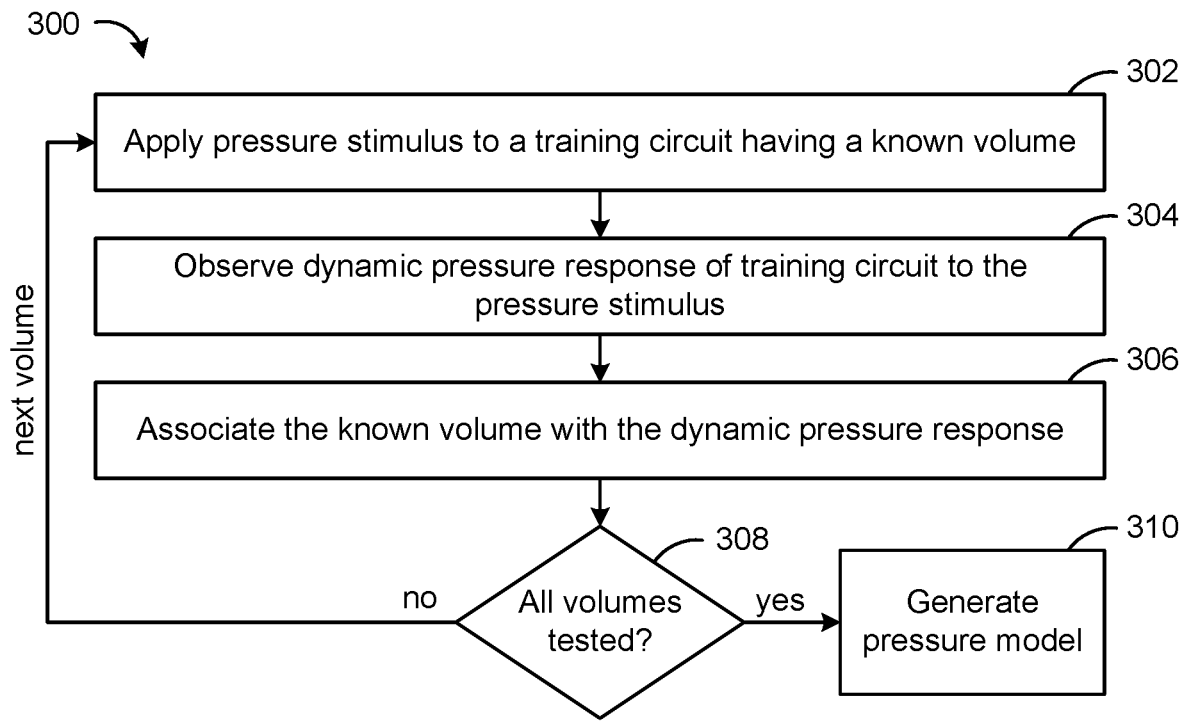
FIG. 8 is a flowchart of a process for generating a pressure response model that relates dynamic pressure response parameters to wound volume, according to an exemplary embodiment.

Referring now to FIG. 8, a flowchart of a process 300 for generating a pressure model is shown, according to an exemplary embodiment. Process 300 can be performed by one or more components of therapy device 102 to create a model that characterizes the dynamic pressure response of a training circuit and/or negative pressure circuit. For example, process 300 can be performed by controller 118, pneumatic pump 120, valve 132, and/or pressure sensors 130 and/or 113. In some embodiments, process 300 is executed by testing procedure controller 148 and model generator 154.

Process 300 is shown to include applying a pressure stimulus to a training circuit having a known volume (step 302). The training circuit may include one or more components of therapy device 102 (e.g., conduit 136, removed fluid canister 106, etc.) and/or other components of system 100 (e.g., tubing 110, wound dressing 112). Under wound treatment conditions, wound dressing 112 would normally be applied to a patient's skin 116 surrounding a wound 114. However, the training circuit may replace wound 114 with a training device having a known volume. Step 302 may include instructing valve 132 to close and operating pneumatic pump 120 to establish negative pressure within the training circuit. Once the negative pressure has been established, pneumatic pump 120 may be deactivated. Step 302 may include causing valve 132 to open for a predetermined amount of time and then closing valve 132 after the predetermined amount of time has elapsed.

Process 300 is shown to include observing the dynamic pressure response of the training circuit to the pressure stimulus (step 304) and associating the known volume of the training circuit with the dynamic pressure response (step 306). Step 304 may include monitoring the pressure of the training circuit over time using pressure measurements recorded by pressure sensors 130 and/or 113. The dynamic pressure response may be characterized by a variety of parameters including, for example, a depth of purge parameter, a rebound parameter, a delta parameter, and a leak rate parameter, as previously described. Step 306 may include storing the values of the parameters of the dynamic pressure response as input training data and storing the known volume of the training circuit as output training data that corresponds to the input training data.

Process 300 is shown to include determining whether all volumes have been tested (step 308). If not all volumes have been tested (i.e., the result of step 308 is "no"), the training device to which therapy device 102 is connected can be replaced with a different training device having a different known volume. Steps 302-306 can then be repeated to apply the pressure stimulus to apply the pressure stimulus and observe the dynamic pressure response of the training circuit for each known volume. Each set of dynamic pressure response parameters can be stored as input training data and each set and the corresponding known volume can be stored as output training data.

Once all volume have been tested (i.e., the result of step 308 is "yes"), process 300 may proceed to generating a pressure model (step 310). Step 310 may include using any of a variety of model generation techniques to construct a model (i.e., a mathematical model) that relates the values of the dynamic pressure response parameters to the corresponding volume in the set of training data.

In some embodiments, the model generated in step 310 is a polynomial approximation model. Step 310 may include performing a curve fitting process such as polynomial regression using any of a variety of regression techniques. Examples of regression techniques which can be used in step 310 include least squares, ordinary least squares, linear least squares, partial least squares, total least squares, generalized least squares, weighted least squares non-linear least squares, non-negative least squares, iteratively reweighted least squares, ridge regression, least absolute deviations, Bayesian linear regression, Bayesian multivariate linear regression, etc.

In some embodiments, the model generated in step 310 is a neural network model. Step 310 may include using any of a variety of machine learning techniques to generate a neural network model that relates the values of the dynamic pressure response parameters to the corresponding volume in the set of training data. Examples of machine learning techniques which can be used in step 310 include decision tree learning, association rule learning, artificial neural networks, deep learning, inductive logic programming, support vector machines, clustering, Bayesian networks, reinforcement learning, representation learning, similarity and metric learning, sparse dictionary learning, genetic algorithms, rule-based machine learning, etc. The pressure model can then be stored for use in estimating the volume of wound 114.

Figure 9:
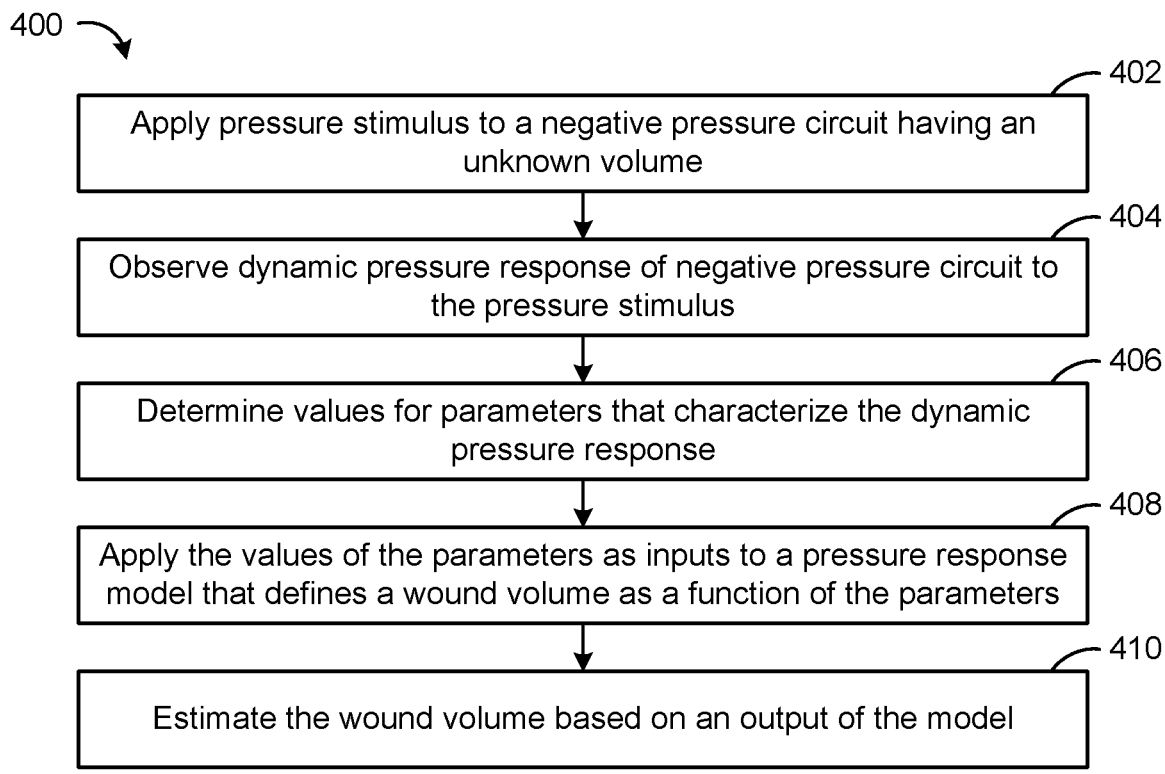
FIG. 9 is a flowchart of a process for estimating wound volume by applying a pressure stimulus to a negative pressure circuit and observing the dynamic pressure response, according to an exemplary embodiment.

Referring now to FIG. 9, a flowchart of a process 400 for estimating the volume of a wound is shown, according to an exemplary embodiment. Process 400 can be performed by one or more components of therapy device 102 estimate the volume of wound 114. For example, process 400 can be performed by controller 118, pneumatic pump 120, valve 132, and/or pressure sensors 130 and/or 113. In some embodiments, process 400 is executed by testing procedure controller 148 and wound volume estimator 156.

Process 400 is shown to include applying a pressure stimulus to a negative pressure circuit having an unknown volume (step 402). The negative pressure circuit may include one or more components of therapy device 102 (e.g., conduit 136, removed fluid canister 106, etc.) and/or other components of system 100 (e.g., tubing 110, wound dressing 112, wound 114). Under wound treatment conditions, wound dressing 112 may be applied to a patient's skin 116 surrounding wound 114. Accordingly, the volume of wound 114 forms part of the negative pressure circuit. Step 402 may include instructing valve 132 to close and operating pneumatic pump 120 to establish negative pressure within the negative pressure circuit. Once the negative pressure has been established, pneumatic pump 120 may be deactivated. Step 402 may include causing valve 132 to open for a predetermined amount of time and then closing valve 132 after the predetermined amount of time has elapsed. In some embodiments, step 402 includes executing the passive testing procedure and/or the active testing procedure, as described with reference to FIGS. 6A-6B.

Process 400 is shown to include observing the dynamic pressure response of the negative pressure circuit to the pressure stimulus (step 404) and determining values for parameters that characterize the dynamic pressure response (step 406). Step 404 may include monitoring the pressure of the negative pressure circuit over time using pressure measurements recorded by pressure sensors 130 and/or 113. The dynamic pressure response may be characterized by a variety of parameters including, for example, a depth of purge parameter, a rebound parameter, a delta parameter, and a leak rate parameter, as previously described. Step 406 may include storing the values of the parameters of the dynamic pressure response.

Process 400 is shown to include applying the values of the parameters as inputs to a pressure response model that defines a wound volume as a function of the parameters (step 408). In some embodiments, the pressure response model is the model created by performing process 300 (e.g., by performing a regression process or machine learning process using training data collected using the training circuits). The model may include a polynomial approximation model, a neural network model, or any other model that relates the observed parameters to the volume of the negative pressure circuit and/or the volume of wound 114.

Process 400 is shown to include estimating the volume of the wound based on an output of the model (step 410). In some embodiments, the output of the pressure response model is the estimated volume of wound 114. Accordingly, the output of the pressure response model can be used as the estimated wound volume. In other embodiments, the output of the pressure response model is the estimated volume of the negative pressure circuit. If the output of the pressure response model is the estimated volume of the negative pressure circuit, step 410 may include subtracting known volumes of other components of the negative pressure circuit to isolate the estimated volume of wound 114. For example, step 410 may include subtracting the known volumes of conduit 136, removed fluid canister 106, tubing 110, and/or wound dressing 112 such that the only volume remaining is the volume of wound 114.

In some embodiments, the volume of removed fluid canister 106 that forms part of the negative pressure circuit is limited to the volume of the air within canister 106. The volume of the air within canister 106 may vary based on the level of removed fluid 107 within canister 106. In some embodiments, removed fluid canister 106 includes a sensor (e.g., a level sensor, a weight sensor, etc.) that operates to record the level of removed fluid 107 within canister 106. The observed level of removed fluid 107 can then be used to estimate the air volume within canister 106. In other embodiments, the volume of air within canister 106 can be estimated by performing a dead-space detection process. An example of a dead-space detection process which can be used to estimate the volume of air within canister 106 is described in detail in U.S. Provisional Patent Application No. 62/577,579 filed Oct. 26, 2017, the entire disclosure of which is incorporated by reference herein.

Figure 10:
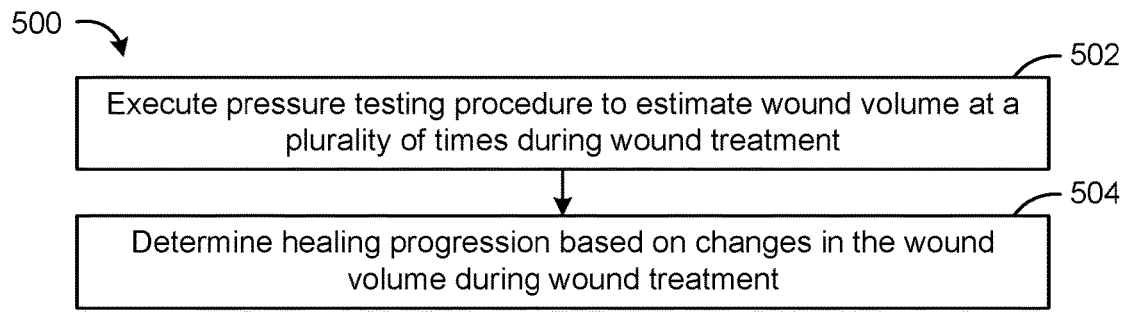
FIG. 10 is a flowchart of a process for monitoring healing progression over time based on a set of wound volume estimates, according to an exemplary embodiment.

Referring now to FIG. 10, a flowchart of a process 500 for monitoring healing progression over time is shown, according to an exemplary embodiment. Process 500 can be performed by one or more components of therapy device 102 to assess healing progression based on the volume of wound 114. For example, process 500 can be performed by controller 118, pneumatic pump 120, valve 132, and/or pressure sensors 130 and/or 113.

Process 500 is shown to include executing a pressure testing procedure to estimate wound volume at a plurality of times during wound treatment (step 502). Step 502 may include performing process 400 multiple times during wound treatment (e.g., once per day). Each time process 400 is performed, the volume of wound 114 may be estimated. Each estimate of the wound volume can be stored along with the time at which the estimate was obtained. The pairs of time and estimated wound volume can be stored as data points within the memory of therapy device 102 and/or presented to a user as an output of therapy device 102 (e.g., via communications interface 124 or user interface 126). In some embodiments, the estimated wound volume can be plotted as a function of time, as shown in FIG. 11.

Process 500 is shown to include determining healing progression based on changes in the wound volume during wound treatment (step 504). Step 504 may include comparing a current estimate of the wound volume to one or more previous estimates of the wound volume to identify a change in the wound volume. In some embodiments, step 504 includes determining a rate at which wound 114 is healing based on the changes in the wound volume over time. In some embodiments, step 504 includes extrapolating or predicting a time at which wound 114 will be fully healed based on a series of wound volume estimates. For example, step 504 may include predicting a time at which the estimated wound volume will reach zero (or another threshold value) based on the series of wound volume estimates obtained in step 502.

Figure 11:
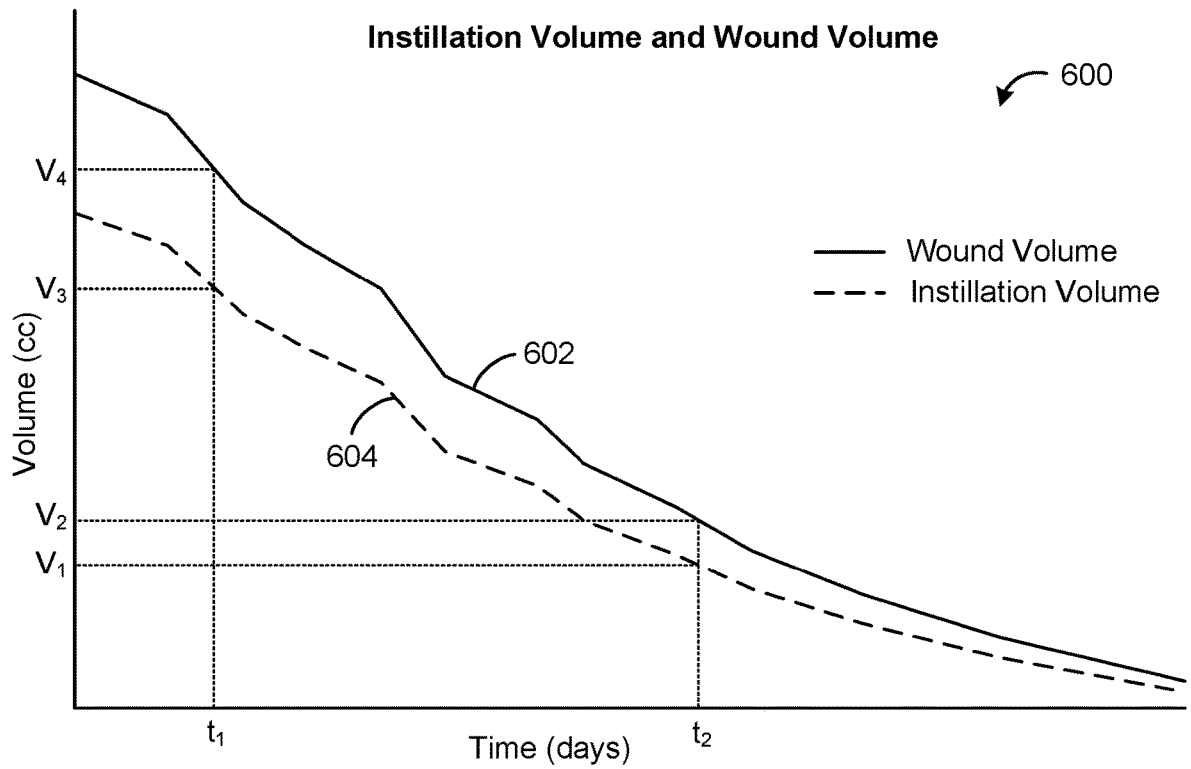
FIG. 11 is a graph illustrating wound volume and instillation fluid volume over time, according to an exemplary embodiment.
Figure 12:
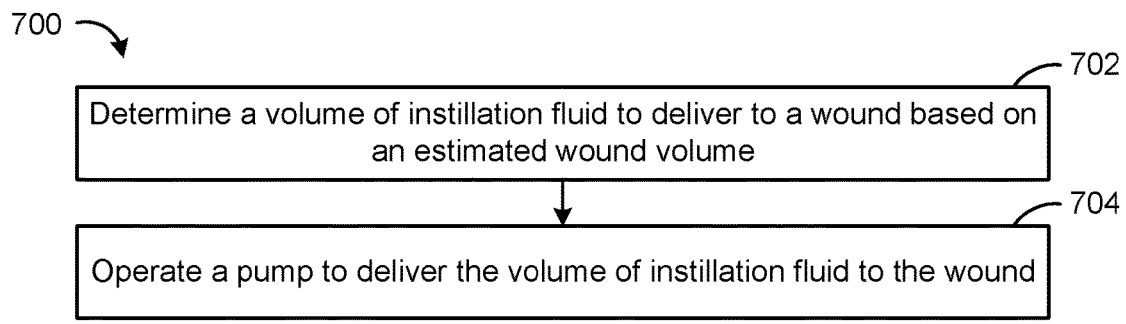
FIG. 12 is a flowchart of a process for determining an amount of instillation fluid to deliver to a wound based on an estimated wound volume, according to an exemplary embodiment.

Referring now to FIGS. 11-12, a graph 600 and flowchart 700 illustrating an application of the wound volume estimates are shown, according to an exemplary embodiment. Controller 118 can use the estimated wound volume to calculate a volume of instillation fluid 105 to deliver to wound 114 (step 702). In some embodiments, controller 118 calculates the volume of instillation fluid 105 to deliver to wound 114 by multiplying the estimated wound volume by a fluid instillation factor. The fluid instillation factor may be less than one (i.e., between zero and one) such that the calculated volume of instillation fluid 105 is less than the volume of wound 114. In some embodiments, the fluid instillation factor is between approximately 0.2 and approximately 0.8. However, it is contemplated that the fluid instillation factor can have any value in various alternative embodiments.

In graph 600, line 602 represents the estimated volume of wound 114 as a function of time, whereas line 604 represents the calculated volume of instillation fluid 105 to deliver to wound 114 over time. At time $t_1$, the estimated volume of wound 114 is $V_4$. The estimated wound volume $V_4$ at time $t_1$ can be multiplied by the fluid instillation factor F (e.g., F=0.8) to calculate the volume of instillation fluid 105 $V_3$ to deliver to wound 114 at time $t_1$ (i.e., $V_4*F=V_3$). As wound 114 heals, the estimated volume of wound 114 decreases and reaches a value of $V_2$ at time $t_2$. The estimated wound volume $V_2$ at time $t_2$ can be multiplied by the fluid instillation factor F to calculate the volume of instillation fluid 105 $V_1$ to deliver to wound 114 at time $t_2$ (i.e., $V_2*F=V_1$).

Controller 118 can then operate a pump to deliver the calculated volume of instillation fluid 105 to wound 114 (step 704). Step 704 can include operating instillation pump 122 to draw instillation fluid 105 from instillation fluid canister 104 and deliver instillation fluid 105 to wound 114 via tubing 109 and 108. In some embodiments, the calculated volume of instillation fluid 105 is also used to control the operation of pneumatic pump 120. For example, controller 118 can operate pneumatic pump 120 to remove the volume of instillation fluid 105 from wound 114 via tubing 110. The amount of time that pneumatic pump 120 operates may be a function of the volume of instillation fluid 105 that was delivered to wound 114.

Wound Therapy Graph

Figure 13:
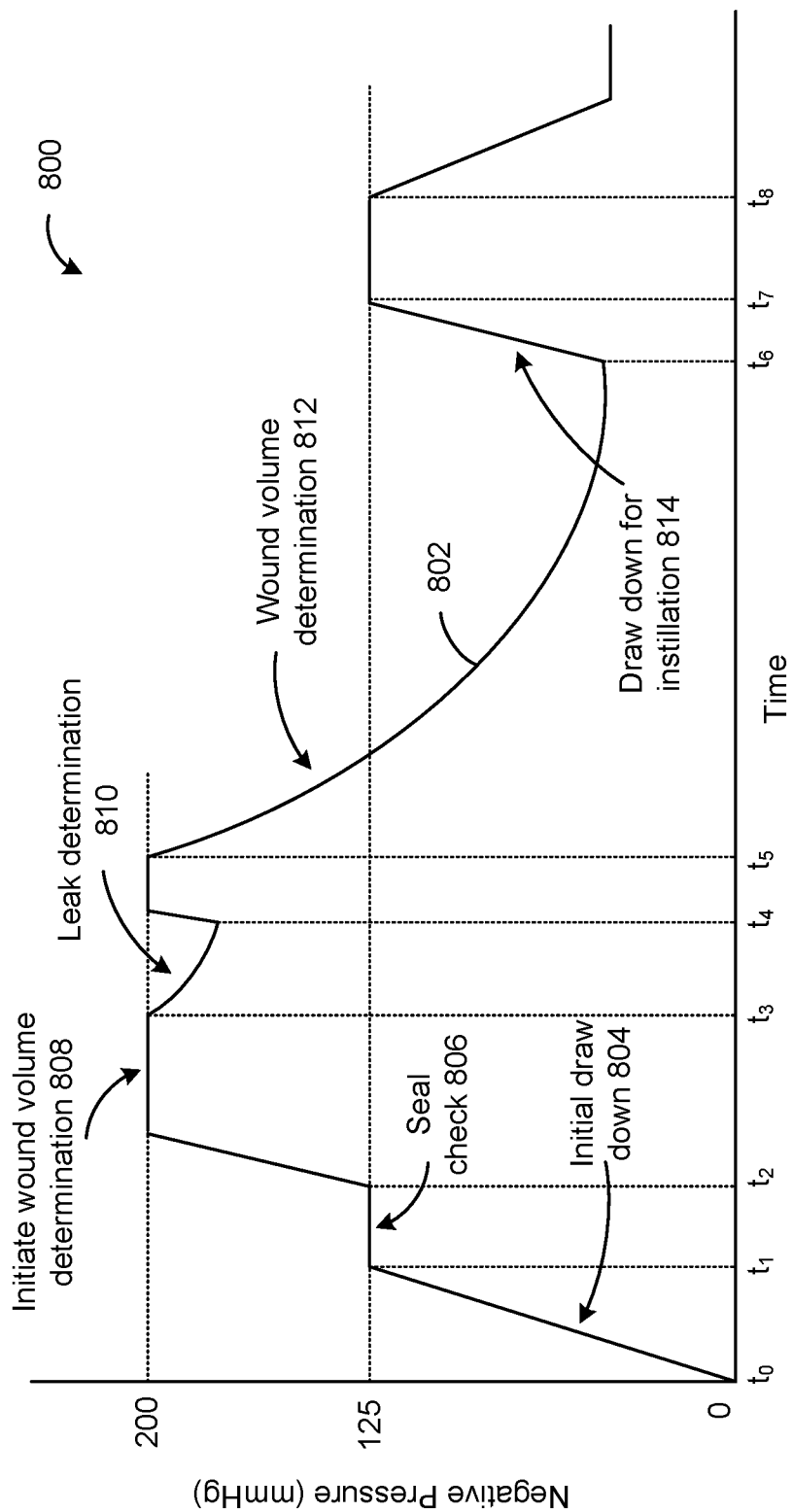
FIG. 13 is a graph illustrating a wound therapy process including leak rate determination, wound volume determination, and fluid instillation stages, according to an exemplary embodiment.

Referring now to FIG. 13, a graph 800 illustrating several stages of a wound therapy process is shown, according to an exemplary embodiment. The wound therapy process illustrated in FIG. 13 can be performed by one or more components of therapy device 102 as previously described. Line 802 represents the negative pressure within the negative pressure circuit at each stage of the wound therapy process.

At time $t_0$, therapy device 102 begins operating pneumatic pump 120 to reduce the negative pressure within the negative pressure circuit during an initial draw down stage 804 that occurs between time $t_0$ and $t_1$. At time $t_1$, the negative pressure within the negative pressure circuit reaches approximately 125 mmHg below atmospheric pressure and pneumatic pump 120 is deactivated.

Between times $t_1$ and $t_2$, negative pressure within the negative pressure circuit is monitored using measurements from pressure sensors 130 and/or 113 during a seal check stage 806. A substantial change in the pressure between times $t_1$ and $t_2$ may indicate that the seal between wound dressing 112 and the patient's skin is not airtight whereas a substantially constant pressure between times $t_1$ and $t_2$ may indicate that wound dressing 112 is properly sealed to the patient's skin.

At time $t_2$, pneumatic pump 120 is activated until the negative pressure within the negative pressure circuit is reduced to approximately 200 mmHg below atmospheric pressure. Upon reaching a negative pressure of 200 mmHg, pneumatic pump 120 is deactivated and a wound volume determination stage 808 is initiated. Pneumatic pump 120 may be intermittently activated during stage 808 to maintain the negative pressure at approximately 200 mmHg and compensate for any leakage of air into the negative pressure circuit.

At time $t_3$, pneumatic pump 120 is deactivated and a leak determination stage 810 begins. Between times $t_3$ and $t_4$, the negative pressure within the negative pressure circuit is monitored to determine a rate at which air leaks into the negative pressure circuit. At time $t_4$, pneumatic pump 120 is reactivated to reduce the negative pressure back to approximately 200 mmHg. Pneumatic pump 120 may be intermittently activated between time $t_4$ and $t_5$ to maintain the negative pressure at approximately 200 mmHg and compensate for any leakage of air into the negative pressure circuit.

At time $t_5$, pneumatic pump 120 is deactivated and a wound volume determination stage 812 begins. During wound volume determination stage 812, therapy device 102 may perform one or more of the pressure testing procedures described with reference to FIGS. 6A-6D. The time ranges shown in graphs 200, 210, 220, and 230 may occur entirely between times $t_5$ and $t_6$ in graph 800.

At time $t_6$, pneumatic pump 120 is activated and the negative pressure is reduced to approximately 125 mmHg below atmospheric pressure during a draw down for instillation stage 814. Upon reaching approximately 125 mmHg of negative pressure at time $t_7$, pneumatic pump 120 is deactivated. Pneumatic pump 120 may be intermittently activated between times $t_7$ and $t_8$ to maintain the negative pressure at approximately 125 mmHg and compensate for any leakage of air into the negative pressure circuit. Between times $t_7$ and $t_8$, instillation fluid 105 may be delivered to wound 114.

Configuration of Exemplary Embodiments

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures show a specific order of method steps, the order of the steps may differ from what is depicted. Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A wound therapy system comprising:
   a negative pressure circuit configured to apply negative pressure to a wound;
   a pump fluidly coupled to the negative pressure circuit and operable to control the negative pressure within the negative pressure circuit;
   a pressure sensor configured to measure the negative pressure within the negative pressure circuit or at the wound; and
   a controller communicably coupled to the pump and the pressure sensor, the controller configured to:
      execute a pressure testing procedure comprising applying a pressure stimulus to the negative pressure circuit;
      observe a dynamic pressure response of the negative pressure circuit to the pressure stimulus using pressure measurements recorded by the pressure sensor, the dynamic pressure response characterized by a pressure change within the negative pressure circuit while the pump is inactive; and
      estimate a wound volume of the wound based on the dynamic pressure response.

2. The wound therapy system of claim 1, wherein the negative pressure circuit comprises:
   a wound dressing sealable to skin surrounding the wound;
   at least one of an instillation fluid canister containing instillation fluid for delivery to the wound or a removed fluid canister containing fluid removed from the wound; and
   tubing fluidly connecting the instillation fluid canister or the removed fluid canister with the wound dressing.

3. The wound therapy system of claim 1, wherein the testing procedure comprises:
   operating the pump to establish the negative pressure within the negative pressure circuit; and
   applying the pressure stimulus after the negative pressure has been established within the negative pressure circuit.

4. The wound therapy system of claim 1, further comprising a valve coupled to the negative pressure circuit and operable to controllably vent the negative pressure circuit.

5. The wound therapy system of claim 4, wherein applying the pressure stimulus comprises:
   opening the valve to allow airflow into the negative pressure circuit for a predetermined amount of time; and
   closing the valve after the predetermined amount of time has elapsed.

6. The wound therapy system of claim 5, wherein applying the pressure stimulus further comprises:
   waiting for another predetermined amount of time after closing the valve; and
   repeating the opening, closing, and waiting steps until the negative pressure reaches a threshold pressure value.

7. The wound therapy system of claim 5, wherein applying the pressure stimulus further comprises operating the pump while the valve is closed to mitigate air leakage into the negative pressure circuit.

8. The wound therapy system of claim 5, wherein the dynamic pressure response of the negative pressure circuit is characterized by a depth of purge parameter defined as a difference between:
   a measured value of the negative pressure before the valve is opened; and
   a measured value of the negative pressure while the valve is open.

9. The wound therapy system of claim 5, wherein the dynamic pressure response of the negative pressure circuit is characterized by a rebound parameter defined as a difference between:
   a measured value of the negative pressure after the valve is closed; and
   a measured value of the negative pressure while the valve is open.

10. The wound therapy system of claim 5, wherein the dynamic pressure response of the negative pressure circuit is characterized by a delta parameter defined as a difference between:
    a measured value of the negative pressure before the valve is opened; and
    a measured value of the negative pressure after the valve is closed.

11. The wound therapy system of claim 5, wherein the dynamic pressure response of the negative pressure circuit is characterized by a leak rate parameter defined as a rate at which the negative pressure changes while the valve is closed.

12. The wound therapy system of claim 1, further comprising an orifice located along the negative pressure circuit and configured to allow air to leak into the negative pressure circuit at a known rate.

13. The wound therapy system of claim 12, wherein applying the pressure stimulus comprises:
    operating the pump to achieve a predetermined negative pressure within the negative pressure circuit; and
    deactivating the pump upon reaching the predetermined negative pressure within the negative pressure circuit.

14. The wound therapy system of claim 1, wherein estimating the wound volume based on the dynamic pressure response comprises:
    determining values for one or more parameters that characterize the dynamic pressure response; and
    applying the values of the one or more parameters as inputs to a model that defines a relationship between the one or more parameters and the wound volume.

15. The wound therapy system of claim 14, wherein the model that defines the relationship between the one or more parameters and the wound volume is a polynomial approximation model.

16. The wound therapy system of claim 14, wherein the model that defines the relationship between the one or more parameters and the wound volume is a neural network.

17. The wound therapy system of claim 14, wherein the controller is configured to generate the model that defines the relationship between the one or more parameters and the wound volume by:
    executing a training procedure comprising applying the pressure stimulus to training circuit having a known volume;
    observing a dynamic pressure response of the training circuit to the pressure stimulus using pressure measurements recorded by the pressure sensor; and
    associating the known volume with the dynamic pressure response of the training circuit.

18. The wound therapy system of claim 17, wherein generating the model further comprises:
    repeating the training procedure for a plurality of known volumes;

observing the dynamic pressure response of the training circuit for each of the plurality of known volumes; and generating a correlation between the plurality of known volumes and the dynamic pressure response of the training circuit.

19. The wound therapy system of claim 1, wherein the controller is configured to:
execute the pressure testing procedure, observe the dynamic pressure response, and estimate the wound volume at a plurality of times during wound treatment; and
determine healing progression based on changes in the wound volume during wound treatment.

20. The wound therapy system of claim 1, wherein the controller is configured to:
determine a volume of instillation fluid to deliver to the wound based on the estimated wound volume; and
operate the pump to deliver the volume of instillation fluid to the wound.

21. The wound therapy system of claim 20, wherein the controller is configured to determine the volume of instillation fluid to deliver to the wound by multiplying the estimated wound volume by a fluid instillation factor.

22. The wound therapy system of claim 21, wherein the fluid instillation factor is less than one such that less than the total wound volume is filled with the instillation fluid.

23. The wound therapy system of claim 21, wherein the fluid instillation factor is between approximately 0.2 and approximately 0.8.

24. A method for estimating a wound volume of a wound, the method comprising:
applying negative pressure to a wound using a negative pressure circuit;
operating a pump fluidly coupled to the negative pressure circuit to control the negative pressure within the negative pressure circuit;
measuring the negative pressure within the negative pressure circuit or at the wound;
executing a pressure testing procedure comprising applying a pressure stimulus to the negative pressure circuit;
observing a dynamic pressure response of the negative pressure circuit to the pressure stimulus using measurements of the negative pressure, the dynamic pressure response characterized by a pressure change within the negative pressure circuit while the pump is inactive; and
estimating the wound volume based on the dynamic pressure response.

25. The method of claim 24, wherein the negative pressure circuit comprises:
a wound dressing sealable to skin surrounding the wound;
at least one of an instillation fluid canister containing instillation fluid for delivery to the wound or a removed fluid canister containing fluid removed from the wound; and
tubing fluidly connecting the instillation fluid canister or the removed fluid canister with the wound dressing.

26. The method of claim 24, wherein the testing procedure comprises:
operating the pump to establish the negative pressure within the negative pressure circuit; and
applying the pressure stimulus after the negative pressure has been established within the negative pressure circuit.

27. The method of claim 24, further comprising operating a valve coupled to the negative pressure circuit to controllably vent the negative pressure circuit.

28. The method of claim 27, wherein applying the pressure stimulus comprises:
opening the valve to allow airflow into the negative pressure circuit for a predetermined amount of time; and
closing the valve after the predetermined amount of time has elapsed.

29. The method of claim 28, wherein applying the pressure stimulus further comprises:
waiting for another predetermined amount of time after closing the valve; and
repeating the opening, closing, and waiting steps until the negative pressure reaches a threshold pressure value.

30. The method of claim 28, wherein applying the pressure stimulus further comprises operating the pump while the valve is closed to mitigate air leakage into the negative pressure circuit.

31. The method of claim 28, wherein the dynamic pressure response of the negative pressure circuit is characterized by a depth of purge parameter defined as a difference between:
a measured value of the negative pressure before the valve is opened; and
a measured value of the negative pressure while the valve is open.

32. The method of claim 28, the dynamic pressure response of the negative pressure circuit is characterized by a rebound parameter defined as a difference between:
a measured value of the negative pressure after the valve is closed; and
a measured value of the negative pressure while the valve is open.

33. The method of claim 28, wherein the dynamic pressure response of the negative pressure circuit is characterized by a delta parameter defined as a difference between:
a measured value of the negative pressure before the valve is opened; and
a measured value of the negative pressure after the valve is closed.

34. The method of claim 28, wherein the dynamic pressure response of the negative pressure circuit is characterized by a leak rate parameter defined as a rate at which the negative pressure changes while the valve is closed.

35. The wound therapy system of claim 1, wherein the controller is configured to determine the pressure change that characterizes the dynamic pressure response by comparing a first pressure measurement recorded by the pressure sensor at a first time and a second pressure measurement recorded by the pressure sensor at a second time, wherein the pump is inactive between the first time and the second time.

36. The method of claim 24, comprising determining the pressure change that characterizes the dynamic pressure response by comparing a first pressure measurement recorded by the pressure sensor at a first time and a second pressure measurement recorded by the pressure sensor at a second time, wherein the pump is inactive between the first time and the second time.

* * * * *